United States Patent
Yoshino

(10) Patent No.: US 8,724,015 B2
(45) Date of Patent: May 13, 2014

(54) IMAGE PROCESSING APPARATUS, IMAGE PROCESSING METHOD, IMAGING APPARATUS, AND INFORMATION STORAGE MEDIUM

(75) Inventor: Koichiro Yoshino, Tokyo (JP)

(73) Assignee: Olympus Corporation, Tokyo (JP)

(*) Notice: Subject to any disclaimer, the term of this patent is extended or adjusted under 35 U.S.C. 154(b) by 338 days.

(21) Appl. No.: 13/198,350

(22) Filed: Aug. 4, 2011

(65) Prior Publication Data
US 2012/0033105 A1 Feb. 9, 2012

(30) Foreign Application Priority Data
Aug. 4, 2010 (JP) ................................. 2010-175623

(51) Int. Cl.
*H04N 5/232* (2006.01)
*G03B 13/00* (2006.01)

(52) U.S. Cl.
USPC .......................................... 348/353; 348/349

(58) Field of Classification Search
USPC ................................................. 348/349, 353
See application file for complete search history.

(56) References Cited

U.S. PATENT DOCUMENTS

| | | | |
|---|---|---|---|
| 2007/0126921 A1* | 6/2007 | Gallagher et al. | 348/362 |
| 2008/0107350 A1 | 5/2008 | Guichard et al. | |
| 2008/0158377 A1 | 7/2008 | Chanas et al. | |
| 2009/0096898 A1 | 4/2009 | Sambongi | |
| 2011/0019065 A1 | 1/2011 | Chanas et al. | |
| 2011/0109749 A1 | 5/2011 | Chanas et al. | |
| 2011/0249173 A1* | 10/2011 | Li et al. | 348/349 |

FOREIGN PATENT DOCUMENTS

| | | |
|---|---|---|
| JP | 4-71070 A | 3/1992 |
| JP | 5-79838 A | 3/1993 |
| JP | 05-302831 | 11/1993 |
| JP | 7-135595 A | 5/1995 |
| JP | 09-327037 | 12/1997 |
| JP | 10-9819 A | 1/1998 |
| JP | 2000-276121 | 10/2000 |
| JP | 2002-365713 A | 12/2002 |
| JP | 2005-140943 A | 6/2005 |
| JP | 2008-532449 | 8/2008 |
| JP | 2008-249431 A | 10/2008 |
| JP | 2009-70344 A | 4/2009 |
| JP | 2010-11066 A | 1/2010 |

OTHER PUBLICATIONS

English abstract only of International Patent Publication No. WO2006/095110A2.
Japanese Office Action dated Apr. 1, 2014 from related Japanese Application No. 2010-175623, together with an English language translation.

* cited by examiner

*Primary Examiner* — Anthony J Daniels
(74) *Attorney, Agent, or Firm* — Scully, Scott, Murphy & Presser, PC

(57) ABSTRACT

An image processing apparatus includes an image acquisition section that acquires a plurality of images that differ in in-focus state, a reference point setting section that performs a reference point setting process on each of the plurality of images, the reference point setting process setting a reference point that is set to an attention area, a distance estimation section that estimates distance information about a distance to a corresponding point based on a pixel value corresponding to the reference point, the corresponding point being a point in real space that corresponds to the reference point, and an additional information generation section that generates additional information based on the estimated distance information, the additional information being information that is added to the attention area to which the reference point is set.

20 Claims, 17 Drawing Sheets

FIG. 2

| R(0,0) | Gr(0,1) | R(0,2) | Gr(0,3) | R(0,4) | Gr(0,5) |
|--------|---------|--------|---------|--------|---------|
| Gb(1,0) | B(1,1) | Gb(1,2) | B(1,3) | Gb(1,4) | B(1,5) |
| R(2,0) | Gr(2,1) | R(2,2) | Gr(2,3) | R(2,4) | Gr(2,5) |
| Gb(3,0) | B(3,1) | Gb(3,2) | B(3,3) | Gb(3,5) | B(3,5) |
| R(4,0) | Gr(4,1) | R(4,2) | Gr(4,3) | R(4,5) | Gr(4,5) |
| Gb(5,0) | B(5,1) | Gb(5,2) | B(5,3) | Gb(5,4) | B(5,5) |

DEPTH OF FIELD OF NEAR POINT IMAGE

DEPTH OF FIELD OF FAR POINT IMAGE

DEPTH OF FIELD OF NEAR POINT IMAGE

DEPTH OF FIELD OF FAR POINT IMAGE

DEPTH OF FIELD (B CHANNEL)

DEPTH OF FIELD (G CHANNEL)

DEPTH OF FIELD (R CHANNEL)

IMAGE PROCESSING APPARATUS, IMAGE PROCESSING METHOD, IMAGING APPARATUS, AND INFORMATION STORAGE MEDIUM

Japanese Patent Application No. 2010-175623 filed on Aug. 4, 2010, is hereby incorporated by reference in its entirety.

BACKGROUND

The present invention relates to an image processing apparatus, an image processing method, an imaging apparatus, an information storage medium, and the like.

An imaging apparatus such as an endoscope is desired to generate a deep-focus image in order to facilitate diagnosis performed by a doctor. In order to satisfy such a demand, the depth of field of an endoscope is increased by utilizing an optical system having a relatively large F-number.

In recent years, an imaging element having about several hundred thousand pixels has been used for endoscope systems. The depth of field of the imaging element is determined by the size of the permissible circle of confusion. Since an imaging element having a large number of pixels has a small pixel pitch and a small permissible circle of confusion, the depth of field of the imaging apparatus decreases. In this case, the depth of field may be maintained by reducing the aperture of the optical system, and increasing the F-number of the optical system. According to this method, however, the optical system darkens, and noise increases, so that the image quality deteriorates. Moreover, the effect of diffraction increases as the F-number increases, so that the imaging performance deteriorates. Accordingly, a high-resolution image cannot be obtained even if the number of pixels of the imaging element is increased.

The depth of field may be increased by acquiring a plurality of images that differ in in-focus object plane, and generating a synthetic image by synthesizing only in-focus areas (see JP-A-2000-276121). The depth of field may also be increased by increasing axial chromatic aberration using an optical system, acquiring a plurality of images that differ in in-focus object plane depending on the channel, and processing the resulting images (see JP-T-2008-532449). The depth of field can be increased while maintaining high resolving power by applying such technology to an endoscope system.

SUMMARY

According to one aspect of the invention, there is provided an image processing apparatus comprising:

an image acquisition section that acquires a plurality of images that differ in in-focus state;

a reference point setting section that performs a reference point setting process on each of the plurality of images, the reference point setting process setting a reference point that is set to an attention area;

a distance estimation section that estimates distance information about a distance to a corresponding point based on a pixel value corresponding to the reference point, the corresponding point being a point in real space that corresponds to the reference point; and an additional information generation section that generates additional information based on the estimated distance information, the additional information being information that is added to the attention area to which the reference point is set.

According to another aspect of the invention, there is provided an image processing apparatus comprising:

an image acquisition section that acquires a plurality of images that differ in in-focus state;

a reference point setting section that performs a reference point setting process on each of the plurality of images, the reference point setting process setting a reference point that is set to an attention area;

a contrast information calculation section that calculates contrast information about the reference point based on a pixel value of a pixel of the reference point set by the reference point setting section; and a distance estimation section that estimates distance information about a distance to a corresponding point based on the reference point setting section, the corresponding point being a point in real space that corresponds to the reference point.

According to another aspect of the invention, there is provided an image processing method comprising:

acquiring a plurality of images that differ in in-focus state;

performing a reference point setting process on each of the plurality of images, the reference point setting process setting a reference point that is set to an attention area;

estimating distance information about a distance to a corresponding point based on a pixel value corresponding to the reference point, the corresponding point being a point in real space that corresponds to the reference point; and generating additional information based on the estimated distance information, the additional information being information that is added to the attention area to which the reference point is set.

According to another aspect of the invention, there is provided an imaging apparatus comprising:

an image acquisition section that acquires a plurality of images that differ in in-focus state;

a reference point setting section that performs a reference point setting process on each of the plurality of images, the reference point setting process setting a reference point that is set to an attention area;

a distance estimation section that estimates distance information about a distance to a corresponding point based on a pixel value corresponding to the reference point, the corresponding point being a point in real space that corresponds to the reference point; and an additional information generation section that generates additional information based on the estimated distance information, the additional information being information that is added to the attention area to which the reference point is set.

According to another aspect of the invention, there is provided an information storage medium storing a program that causes a computer to function as:

an image acquisition section that acquires a plurality of images that differ in in-focus state;

a reference point setting section that performs a reference point setting process on each of the plurality of images, the reference point setting process setting a reference point that is set to an attention area;

a distance estimation section that estimates distance information about a distance to a corresponding point based on a pixel value corresponding to the reference point, the corresponding point being a point in real space that corresponds to the reference point; and an additional information generation section that generates additional information based on the estimated distance information, the additional information being information that is added to the attention area to which the reference point is set.

BRIEF DESCRIPTION OF THE DRAWINGS

FIG. 2 shows a configuration example of an imaging element.

FIGS. 13A and 13B are views illustrative of Zn and Zf settings when calculating an in-focus direction and the like.

DESCRIPTION OF EXEMPLARY EMBODIMENTS

Figure 1:
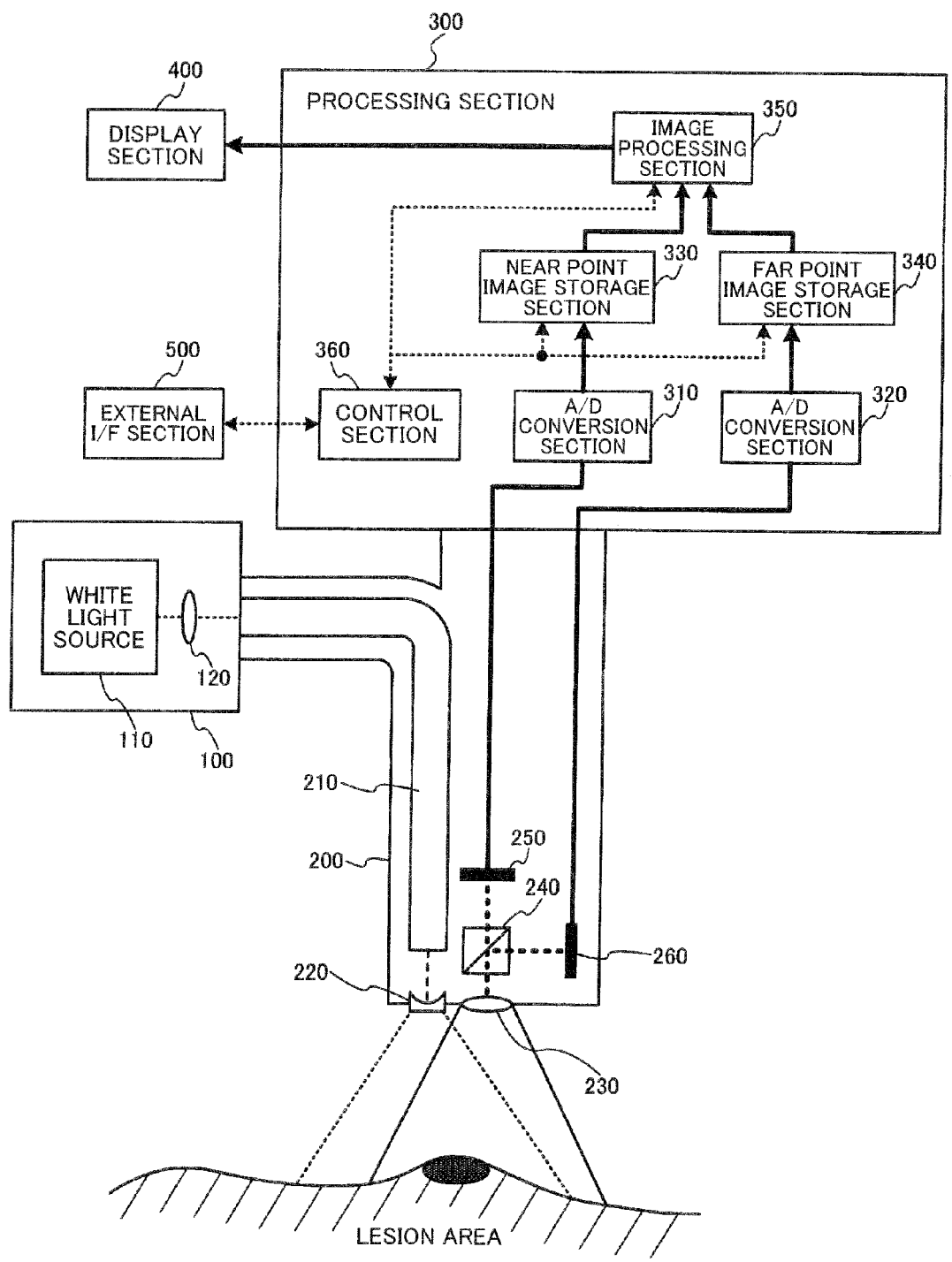
FIG. 1 shows a system configuration example according to one embodiment of the invention.

Several aspects of the invention may provide an image processing apparatus, an image processing method, an imaging apparatus, a program, and the like that provide a doctor with various diagnostic values by estimating the distance to the object from a plurality of images (corresponding to a plurality of channels) that differ in in-focus state (in-focus object plane).

According to one embodiment of the invention, there is provided an image processing apparatus comprising:

an image acquisition section that acquires a plurality of images that differ in in-focus state;

a reference point setting section that performs a reference point setting process on each of the plurality of images, the reference point setting process setting a reference point that is set to an attention area;

a distance estimation section that estimates distance information about a distance to a corresponding point based on a pixel value corresponding to the reference point, the corresponding point being a point in real space that corresponds to the reference point; and an additional information generation section that generates additional information based on the estimated distance information, the additional information being information that is added to the attention area to which the reference point is set.

According to the above configuration, a plurality of images that differ in in-focus state are acquired, and the reference point setting process that sets the reference point to the attention area is performed on each of the plurality of images. The distance to the corresponding point in real space that corresponds to the reference point is then estimated, and the additional information is generated based on the estimated distance information. This makes it possible to generate information useful for the user based on the estimated distance information, and add the generated information to the image information (Le., present the generated information).

According to another embodiment of the invention, there is provided an image processing method comprising:

acquiring a plurality of images that differ in in-focus state;

performing a reference point setting process on each of the plurality of images, the reference point setting process setting a reference point that is set to an attention area;

estimating distance information about a distance to a corresponding point based on a pixel value corresponding to the reference point, the corresponding point being a point in real space that corresponds to the reference point; and generating additional information based on the estimated distance information, the additional information being information that is added to the attention area to which the reference point is set.

According to another embodiment of the invention, there is provided an imaging apparatus comprising:

an image acquisition section that acquires a plurality of images that differ in in-focus state;

a reference point setting section that performs a reference point setting process on each of the plurality of images, the reference point setting process setting a reference point that is set to an attention area;

a distance estimation section that estimates distance information about a distance to a corresponding point based on a pixel value corresponding to the reference point, the corresponding point being a point in real space that corresponds to the reference point; and an additional information generation section that generates additional information based on the estimated distance information, the additional information being information that is added to the attention area to which the reference point is set.

According to another embodiment of the invention, there is provided an information storage medium storing a program that causes a computer to function as:

an image acquisition section that acquires a plurality of images that differ in in-focus state;

a reference point setting section that performs a reference point setting process on each of the plurality of images, the reference point setting process setting a reference point that is set to an attention area;

a distance estimation section that estimates distance information about a distance to a corresponding point based on a pixel value corresponding to the reference point, the corresponding point being a point in real space that corresponds to the reference point; and an additional information generation section that generates additional information based on the estimated distance information, the additional information being information that is added to the attention area to which the reference point is set.

1. Method

A method according to one embodiment of the invention is described below. JP-A-2000-276121 discloses a method that acquires a plurality of images that differ in in-focus state (in-focus object plane), and generates a synthetic image by synthesizing only in-focus areas. According to this method, since a plurality of images that differ in depth of field range can be acquired (see FIG. 3), the depth of field can be increased while maintaining high resolving power by synthesizing the plurality of images utilizing the in-focus areas.

The method that acquires a plurality of images that differ in in-focus state is also advantageous when acquiring distance information about the distance to the object from the imaging apparatus (or the front focal distance of the optical system) by calculating the contrast (sharpness) of each image, for example.

Figure 8E:
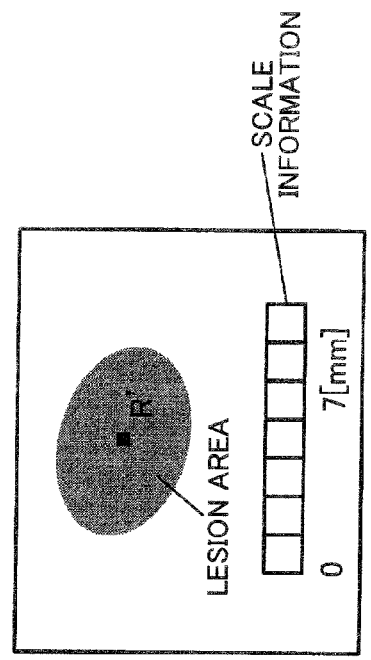
FIGS. 8A to 8E show examples in which additional information is added to an attention area.

The present application proposes a method that adds additional information useful for the user (doctor) to an image based on the distance information about the distance to the object. The additional information may be lesion size information (see FIG. 8C), or scale information that indicates size in real space (see FIG. 8E), for example. The additional information may be in-focus direction information, in-focus indication information, alert information, or the like (see FIGS. 12B to 12E).

Figure 7:
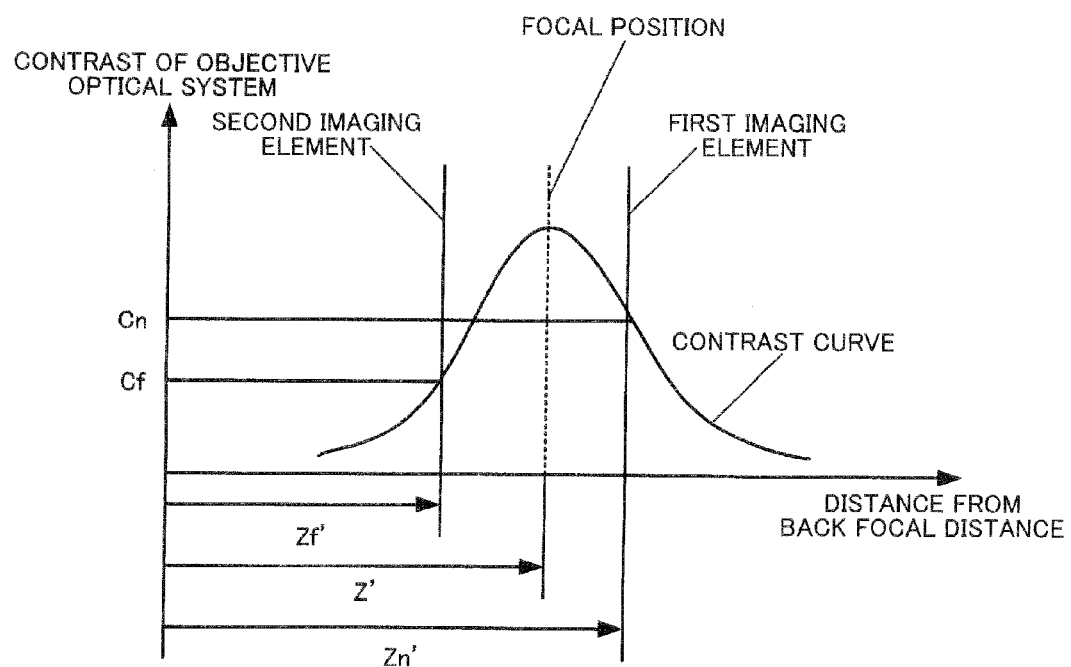
FIG. 7 is a view showing the relationship between the distance from the back focal distance of an objective lens and the contrast of the objective lens at a given spatial frequency.

The distance information may calculated by a method shown in FIG. 7 based on contrast information about a plurality of images and a contrast curve determined by the optical system design, for example.

It is necessary to calculate the three-dimensional coordinates of a corresponding point in real space that corresponds to a reference point on the image in order to display the lesion size information. In this case, the three-dimensional coordinates are calculated by a method shown in FIG. 9. The scale information is generated by calculating a local magnification or the like. The in-focus direction information or the like is generated by comparing the distance information about the distance to the object with the distance from the front focal distance to the end of the depth of field.

A distance information estimation method and an additional information generation method based on the distance information are described in detail in connection with each embodiment.

A first embodiment illustrates a method that utilizes two imaging elements that differ in distance from the objective lens (or distance from the back focal distance) in order to acquire a plurality of images that differ in in-focus state. A second embodiment illustrates a method that produces axial chromatic aberration using an optical system, and acquires a plurality of images that differ in in-focus state depending on the channel (RGB). A third embodiment illustrates a method that acquires a plurality of images that differ in in-focus state by time division using one imaging element by setting the imaging element in a first in-focus state at a first timing, and setting the imaging element in a second in-focus state at a second timing. The first to third embodiments differ in the method of acquiring a plurality of image that differ in in-focus state (the second embodiment differs in the details of a distance estimation method from the first and third embodiments). The first to third embodiments utilize an identical additional information generation/usage method after the distance information has been estimated.

2. First Embodiment

An endoscope system including an image processing apparatus according to the first embodiment of the invention is described below with reference to FIG. 1. The endoscope system according to the first embodiment includes a light source section 100, an imaging section 200, a processing section 300, a display section 400, and an external I/F section 500.

The light source section 100 includes a white light source 110 that emits (generates) white light, and a condenser lens 120 that focuses white light on a light guide fiber 210.

The imaging section 200 is formed to be elongated and flexible (i.e., can be curved) so that the imaging section 200 can be inserted into a body cavity or the like. The imaging section 200 includes the light guide fiber 210 that guides light focused by the light source section 100, an illumination lens 220 that diffuses light that has been guided by the light guide fiber 210, and illuminates an observation target, an objective lens 230 that focuses light reflected by the observation target, a half mirror 240 that separates the optical path of the reflected light, a first imaging element 250, and a second imaging element 260. The first imaging element 250 and the second imaging element 260 include a Bayer color filter array shown in FIG. 2, and color filters Gr and Gb have the same spectral characteristics.

Figure 3A:
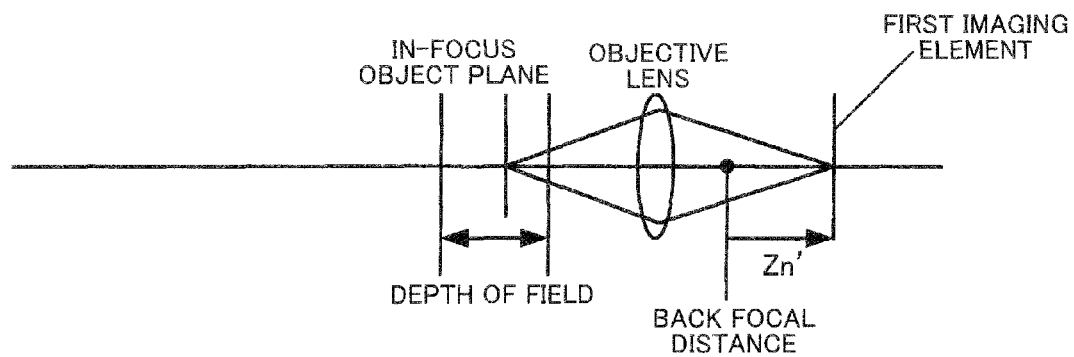
FIG. 3A is a view illustrative of the depth of field of a near point image.
Figure 3B:
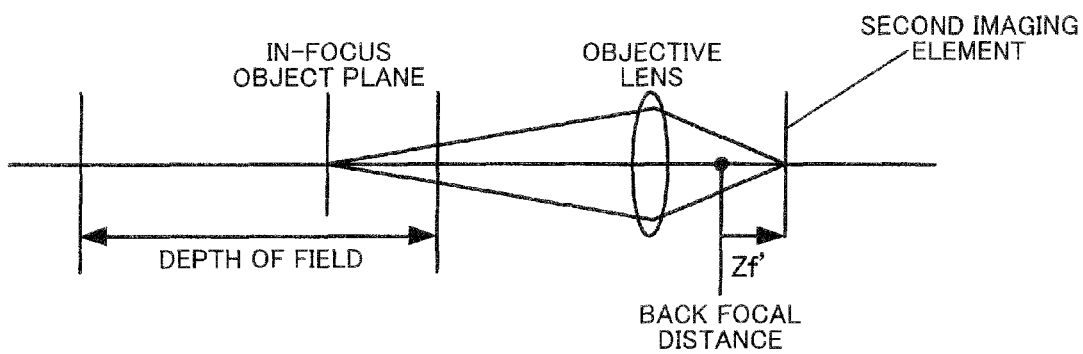
FIG. 3B is a view illustrative of the depth of field of a far point image.

The depth of field of an image acquired (captured) by each imaging element is described below with reference to FIGS. 3A and 3B. $Zn'$ shown in FIG. 3A indicates the distance between the back focal distance of the objective lens and the first imaging element, and $Zf'$ shown in FIG. 3B indicates the distance between the back focal distance of the objective lens and the second imaging element. The first imaging element and the second imaging element are disposed via the half mirror so that the relationship "$Zn'>Zf'$" is satisfied, for example. Therefore, the depth of field range of an image (near point image) acquired by the first imaging element is closer to the objective lens than the depth of field range of an image (far point image) acquired by the second imaging element. The depth of field range of each image can be adjusted by adjusting the values $Zn'$ and $Zf'$.

The processing section 300 includes A/D conversion sections 310 and 320, a near point image storage section 330, a far point image storage section 340, an image processing section 350, and a control section 360. The A/D conversion section 310 converts an analog signal output from the first imaging element 250 into a digital signal, and outputs the digital signal. The A/D conversion section 320 converts an analog signal output from the second imaging element 260 into a digital signal, and outputs the digital signal. The near point image storage section 330 stores the digital signal output from the A/D conversion section 310 as a near point image. The far point image storage section 340 stores the digital signal output from the A/D conversion section 320 as a far point image. The image processing section 350 generates a display image from the stored near point image and far point image, and displays the display image on the display section 400. The details of the image processing section 350 are described later. The display section 400 is a liquid crystal monitor, for example. The display section 400 displays the image output from the image processing section 350. The control section 360 is bidirectionally connected to the near point image storage section 330, the far point image storage section 340, and the image processing section 350, and controls the near point image storage section 330, the far point image storage section 340, and the image processing section 350.

The external I/F section 500 is an interface that allows the user to perform an input operation or the like on the imaging apparatus. The external I/F section 500 includes a power supply switch (power supply ON/OFF switch), a shutter button (photographing operation start button), a mode (e.g., photographing mode) change button, and the like. The external I/F section 500 outputs information input by the user to the control section 360.

The details of the image processing section 350 are described below with reference to FIG. 4. The image processing section 350 includes a reference point setting section 351, a distance estimation section 352, a preprocessing section 353, a synthetic image generation section 354, a post-processing section 355, an additional information generation section 356, and a process section 357. The reference point setting section 351 outputs information about a distance estimation target position on the image to the distance estimation section 352 as coordinate information about a reference point based on a control signal from the control section 360. The details of the reference point setting section 351 are described later.

The preprocessing section 353 performs a preprocess (e.g., OB process, white balance process, and demosaicing process) on the near point image stored in the near point image storage section 330 and the far point image stored in the far point image storage section 340, and outputs the near point image and the far point image to the distance estimation section 352 and the synthetic image generation section 354. The preprocessing section 353 may optionally perform a correction process on optical aberration (e.g., distortion and chromatic aberration of magnification), a noise reduction process, and the like.

The distance estimation section 352 estimates the distance to the object in real space by utilizing the near point image and the far point image output from the preprocessing section 353 based on the coordinate information about the reference point output from the reference point setting section 351, and outputs the distance information or the distance information and the coordinate information about the reference point to the additional information generation section 356. The details of the distance estimation section 352 are described later. The additional information generation section 356 generates additional information using the distance information or the distance information and the coordinate information about the reference point output from the distance estimation section 352 based on a control signal from the control section 360, and outputs the additional information to the process section 357. The details of the additional information generation section 356 are described later.

The synthetic image generation section 354 synthesizes the near point image and the far point image output from the preprocessing section 353 to generate a synthetic image with an increased depth of field, and outputs the synthetic image to the post-processing section 355. The details of the synthetic image generation section 354 are described later. The post-processing section 355 performs a post-process (e.g., color conversion process, grayscale transformation process, edge enhancement process, and scaling process) on the synthetic image output from the synthetic image generation section 354, and outputs the resulting image to the process section 357.

The process section 357 processes the image output from the post-processing section 355 using the additional information output from the additional information generation section 356 based on control information from the control section 360, and outputs the resulting image to the display section 400. The details of the process section 357 are described later.

The details of the process performed by the distance estimation section 352 are described below with reference to FIG. 5. The distance estimation section 352 includes a local area setting section 3521, a contrast information calculation section 3522, and a distance calculation section 3523. The local area setting section 3521 sets a local area to a near point image In and a far point image If input to the distance estimation section 352 based on the coordinates of the reference point output from the reference point setting section 351. As shown in FIG. 6, the local area setting section 3521 sets a 5×5 pixel area around the coordinates (xd, yd) of the reference point as the local area of each image, for example. The contrast information calculation section 3522 calculates the contrast of each image from the local area set to each of the near point image In and the far point image If, and outputs a contrast Cn of the local area of the near point image and a contrast Cf of the local area of the far point image to the distance calculation section.

For example, the contrast information calculation section 3522 calculates gradients $\Delta u$, $\Delta d$, $\Delta l$, and $\Delta r$ of each pixel of the local area set to the near point image In and the far point image If relative to four pixels adjacent to each pixel in the vertical direction or the horizontal direction using the pixel value of the G channel, and calculates the average values $\Delta ave\_In$ and $\Delta ave\_If$ of the gradients of each pixel of the local area in the four directions to determine the contrast Cn and the contrast Cf The contrast information calculation section 3522 may calculate the average value of the edge strength of the local area as the contrast, for example.

The distance calculation section 3523 calculates the distance to the object corresponding to the reference point from the contrast Cn and the contrast Cf FIG. 7 shows an example of a contrast curve that indicates the relationship between the distance from the back focal distance of the objective lens and the contrast of the objective lens at a given spatial frequency. If the distance Z' from the back focal distance to the focal position of the object corresponding to the reference point is determined, the distance Z from the front focal distance to the object corresponding to the reference point can be calculated by the following expression (1). Note that f is the focal length of the objective lens, $$Z \cdot Z' = -f^2 \qquad (1)$$

Since the contrast curve of the objective lens is known from the design data, the distance Z' can be calculated from the contrast Cn of the near point image and the contrast Cf of the far point image corresponding to the reference point. For example, the relationship between the contrast ratio Cn/Cf of the near point image to the far point image and the corresponding distance Z' may be stored as a look-up table, or a function g(x) that approximates the distance Z' as indicated by Z'=g(Cn/Cf) (i.e., a function of the contrast ratio Cn/Cf) may be set in advance. The distance calculation section 3523 can calculate the distance to the object corresponding to the reference point from the contrast Cn and the contrast Cf by performing the above process. The distance Z can be uniquely calculated by the expression (1) when the distance Z' has been calculated. For example, the relationship between the contrast ratio Cn/Cf and the distance Z to the corresponding object may be stored directly as a look-up table, or a function h(x) that approximates the distance Z as indicated by Z=h(Cn/Cf) (i.e., a function of the contrast ratio Cn/Cf) may be set in advance. The contrast difference Cn−Cf or the like may be used as a parameter for calculating the distance Z or Z' instead of the contrast ratio Cn/Cf of the near point image to the far point image.

The details of the process performed by the synthetic image generation section 354 are described below. The near point image input to the synthetic image generation section 354 is referred to as In, and the far point image input to the synthetic image generation section 354 is referred to as If. The synthetic image output from the synthetic image generation section 354 is referred to as Ic. The synthetic image generation section 354 calculates the sharpness of an attention pixel In(x, y) positioned at the coordinates (x, y) of the near point image In and an attention pixel If(x, y) positioned at the coordinates (x, y) of the far point image If from the gradient of the attention pixel relative to an arbitrary peripheral pixel and the edge strength of the attention pixel, for example. The sharpness of the pixel (x, y) of the near point image In is referred to as S_In(x, y), and the sharpness of the pixel (x, y) of the far point image If is referred to as S_If(x, y).

The synthetic image generation section 354 then compares the sharpness S_In(x, y) with the sharpness S_If(x, y). When S_In(x, y)≥S_If(x, y), the value In(x, y) is used as the value Ic(x, y) of the pixel (x, y) of the synthetic image Ic. When S_In(x, y)<S_If(x, y), the value If(x, y) is used as the value Ic(x, y). This makes it possible to extract an in-focus pixel from the near point image In and the far point image If to generate a synthetic image with an increased depth of field.

Several methods that provide a doctor with a diagnostic value by utilizing the distance information calculated by the distance estimation section 352 are described below.

2.1 Display of Lesion Size

Figure 8D:
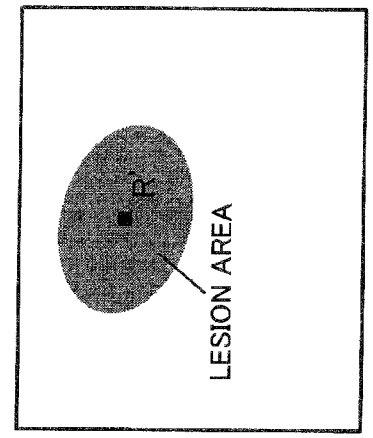

In endoscopic diagnosis, the size of a lesion area is an important index for determining therapeutic strategy and the like. Therefore, it has been desired to easily measure the size of a lesion area. A first method is used to measure the size of a lesion area when an image of a lesion area shown in FIG. 8A is displayed on the display section 400 during endoscopic diagnosis. A mode in which the following process is performed is referred to as a first lesion area measurement mode.

When a lesion area has been found in the first lesion area measurement mode, the doctor designates distance measurement target positions on the image. The following description is given on the assumption that the doctor has designated points A' and B' shown in FIG. 8B as the distance measurement target positions. The distance measurement target positions may be designated by moving a pointer on the image using a keyboard, a mouse, or the like attached to the endoscope system, and pressing an OK button, for example. Alternatively, a monitor having a touch panel function may be used as the display section 400, and the distance measurement target positions may be designated by touching the monitor (image) directly with the finger or using a touch pen.

In the first lesion area measurement mode, the reference point setting section 351 acquires the coordinates (Xa', Ya') and (Xb', Yb') of the designated points A' and B' on the image according to mode information from the control section 360, and outputs the coordinates (Xa', Ya') and (Xb', Yb') to the distance estimation section 352 as the coordinate information about the reference point. The distance estimation section 352 calculates distance information Za about the distance from the front focal distance to a point A on the object corresponding to the point A', and distance information Zb about the distance from the front focal distance to a point B on the object corresponding to the point B' using the above method, and outputs the distance information Za, the distance information Zb, and the coordinate information about the reference point to the additional information generation section 356.

Figure 9B:
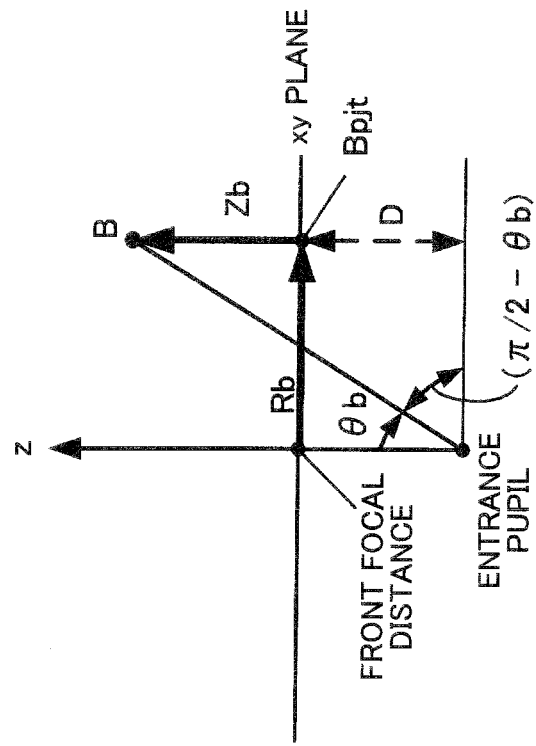
FIGS. 9A and 9B are views illustrative of a method that calculates the coordinates of a corresponding point in real space from the coordinates of a reference point on an image.
Figure 9A:
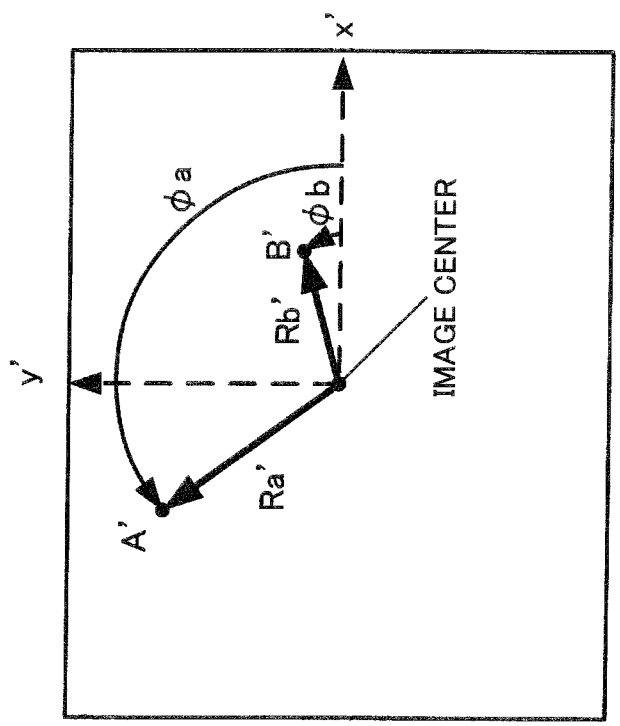

The additional information generation section 356 calculates the three-dimensional coordinates (Xa, Ya, Za) and (Xb, Yb, Zb) of the points A and B from the distance information and the coordinate information about the reference point output from the distance estimation section 352 according to the mode information from the control section 360, and calculates the distance (i.e., the size of the lesion area) between the points A and B in real space using the three-dimensional coordinates (Xa, Ya, Za) and (Xb, Yb, Zb). As shown in FIG. 9A, the x' axis and the y' axis that indicate the position of the reference point on the image extend from the center (i.e., origin) of the image in parallel to the horizontal direction or the vertical direction of the image. The x-axis and the y-axis in real space perpendicularly intersect at the front focal distance, and extend in the same direction as the x' axis and the y' axis, respectively. As shown in FIG. 9B, the Z-axis in real space is a straight line that passes through the front focal distance, and perpendicularly intersects the xy plane. The three-dimensional coordinate value Za of the point A and the three-dimensional coordinate value Zb of the point B indicate the distance from the front focal distance to the object in the Z-axis direction. Therefore, the three-dimensional coordinate value Za and the three-dimensional coordinate value Zb respectively correspond to the distance information Za and the distance information Zb output from the distance estimation section 352.

A method of calculating the three-dimensional coordinates (Xb, Yb, Zb) of the point B is described below with reference to FIGS. 9A and 9B. The additional information generation section 356 calculates the distance (image height) Rb' from the center of the image to the point B' and the angle φb formed by a straight line that passes through the point B' and the center of the image and the x' axis from the coordinates (Xb', Yb') of the point B' on the image.

Figure 10:
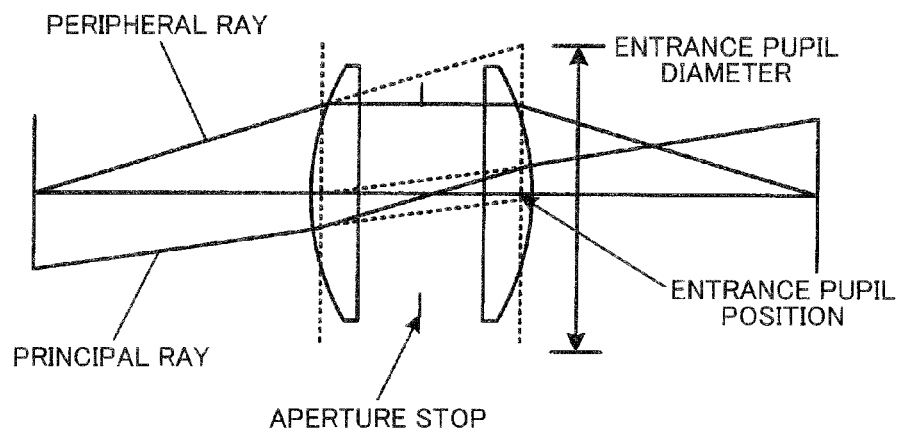
FIG. 10 is a view illustrative of an entrance pupil.

The additional information generation section 356 then calculates an incident angle θb at which a principal ray emitted from the point B enters the entrance pupil in real space using the image height Rb'. Note that the entrance pupil refers to an image of the aperture imaged by the optical system disposed on the side of the object with respect to the aperture. As shown in FIG. 10, the entrance pupil position is a position where the principal ray intersects the optical axis (that coincides with the Z-axis in this example). The distance D from the front focal distance to the entrance pupil is known from the optical system design. The relationship between the image height Rb' and the incident angle θb is known from the performance of the objective lens. Therefore, the spatial position of the point B is uniquely determined (see FIG. 9B) when the incident angle θb has been calculated. When calculating the incident angle θb, the relationship between the image height Rb' and the incident angle θb may be stored as a look-up table, or a function f(x) that approximates the incident angle θb as indicated by θb=f(Rb') (i.e., a function of the image height Rb') may be set in advance, for example.

The additional information generation section 356 then calculates the distance Rb between a point Bpjt obtained by projecting the point B onto the xy plane and the origin of the xy plane by the following expression (2) using the incident angle θb.

$$Rb=(Zb+D)/\tan(\pi/2-\theta b) \qquad (2)$$

Since the angle formed by the x-axis and a straight line that passes through the point Bpjt and the front focal distance in real space is equal to the angle φb, the coordinate values Xb and Yb can be calculated by the following expressions (3) and (4).

$$Xb=Rb\cdot\cos\phi b \qquad (3)$$

$$Yb=Rb\cdot\sin\phi b \qquad (4)$$

The three-dimensional coordinates (Xb, Yb, Zb) of the object in real space that corresponds to the point B can thus be calculated. This also applies to the three-dimensional coordinates (Xa, Ya, Za) of the point A.

The additional information generation section 356 calculates the distance Dsize between the two points by the following expression (5) from the calculated three-dimensional coordinates (Xa, Ya, Za) and (Xb, Yb, Zb), and outputs the distance Dsize to the process section 357 as lesion area size information.

$$Dsize=\sqrt{(Xa-Xb)^2+(Ya-Yb)^2+(Za-Zb)^2} \quad (5)$$

The process section 357 adds the lesion size information output from the additional information generation section 356 to the image output from the post-processing section 355 according to the mode information from the control section 360. For example, the size of the lesion is displayed on the image as a numerical value (see FIG. 8C). The above process makes it possible for the doctor to easily measure the size of the lesion area.

2.2 Display of Scale

A second method that is used to measure the size of a lesion area when an image of a lesion area shown in FIG. 8A is displayed on the display section 400 during endoscopic diagnosis is described below. A mode in which the following process is performed is referred to as a second lesion area measurement mode.

When a lesion area has been found in the second lesion area measurement mode, the doctor designates a representative position of the lesion area on the image. The following description is given on the assumption that the doctor has designated a point R' shown in FIG. 8D as the representative position of the lesion area. The representative position of the lesion area may be designated by moving a pointer on the image using a keyboard, a mouse, or the like attached to the endoscope system, and pressing an OK button, for example. Alternatively, a monitor having a touch panel function may be used as the display section 400, and the representative position of the lesion area may be designated by touching the monitor (image) directly with the finger or using a touch pen.

In the second lesion area measurement mode, the reference point setting section 351 acquires the coordinates (Xr', Yr') of the designated point R' on the image according to the mode information from the control section 360, and outputs the coordinates (Xr', Yr') to the distance estimation section 352 as the coordinate information about the reference point. The distance estimation section 352 calculates distance information Zr about the distance from the front focal distance to a point R on the object corresponding to the point R' in real space using the above method, and outputs the distance information Zr and the coordinate information about the reference point to the additional information generation section 356.

Figure 11:
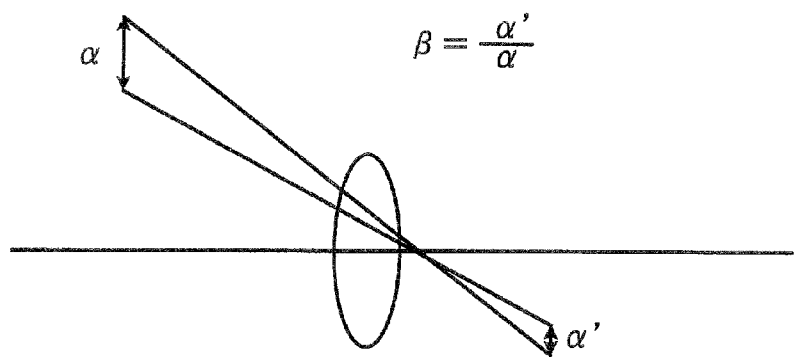
FIG. 11 is a view illustrative of a local magnification.

The additional information generation section 356 calculates a local magnification β of the objective lens at the point R' on the image from the distance information and the coordinate information about the reference point output from the distance estimation section 352 according to the mode information from the control section 360. The local magnification β is indicated by the ratio of the size α' of an image formed by the optical system to the size a of the object (β=α'/α) (see FIG. 11), for example. The local magnification β is calculated by the following expression (6) using the distance Zr to the object output from the distance estimation section 352, for example. Note that f is the focal length of the objective lens.

$$\beta = \sqrt{\frac{f^2}{Zr^2}} \quad (6)$$

Since an objective lens of an endoscope generally undergoes large distortion, the local magnification β differs depending on the position on the image. The relationship between the position on the image and the local magnification β is known from the performance of the objective lens. In this case, the relationship between the position on the image and the local magnification β may be stored as a look-up table, and the local magnification β may be calculated by combining the look-up table and the expression (6). A three-dimensional look-up table that links the local magnification to the position on the image and the distance from the front focal distance to the object may be stored, and the local magnification β may be calculated using the three-dimensional look-up table.

The additional information generation section 356 then generates scale information from the local magnification β. For example, when displaying a scale having a length of L in real space on the image, the additional information generation section 356 calculates the length of the scale on the image by the following expression (7). Note that P is the pixel pitch (i.e., the distance between the pixels (i.e., size per pixel)) of the imaging element. When the post-processing section performs a scaling process, the additional information generation section 356 calculates the length of the scale on the image by the following expression (8) (βzoom is the scaling factor of the scaling process). The additional information generation section 356 then outputs the length of the scale thus calculated to the process section 357 as the scale information.

$$\text{Length of scale on image} = L \cdot \beta / P [\text{pixels}] \quad (7)$$

$$\text{Length of scale on image} = L \cdot \beta \cdot \beta zoom / P [\text{pixels}] \quad (8)$$

The process section 357 adds the scale information output from the additional information generation section 356 to the image output from the post-processing section 355 according to the mode information from the control section 360. For example, a scale image is displayed on the image (see FIG. 8E). Note that the scale information need not necessarily be indicated by a rectangle. The scale information may be indicated by a line segment or an arbitrary shape (e.g., circle) other than a rectangle.

2.3 Indication Information that Indicates In-Focus Direction in Zoom State or the Like Endoscopic diagnosis generally employs a magnifying observation method that utilizes a zoom lens as the objective lens 230, and magnifies a lesion area by bringing the imaging section 200 close to the lesion area. Since the depth of field of the optical system of the endoscope generally becomes very narrow when using the magnifying observation method, it is very difficult to bring the lesion area (i.e., object) into focus. Therefore, it is desired to bring the lesion area into focus as easily as possible. If the imaging section 200 comes in contact with the lesion area, bleeding may occur from the lesion area. Therefore, it is desired to prevent the imaging section 200 from coming in contact with the lesion area. An endoscopic diagnosis method that can meet these demands is described below. A mode in which the following process is performed is referred to as a magnifying observation mode.

Figure 12E:
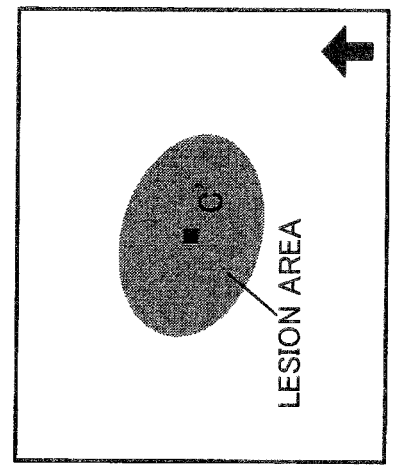
FIGS. 12A to 12E show examples in which additional information is added to an attention area.
Figure 12A:
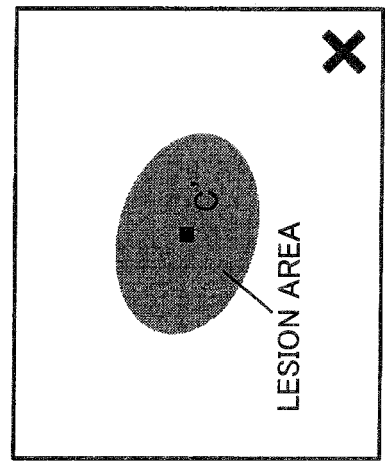
Figure 12B:
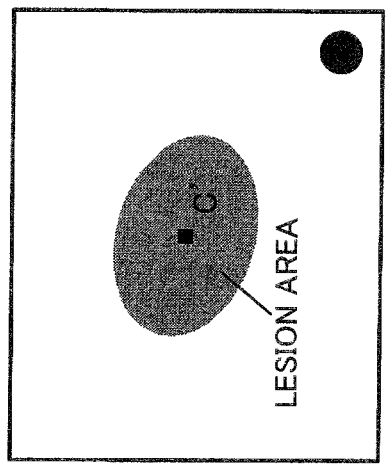
Figure 12C:
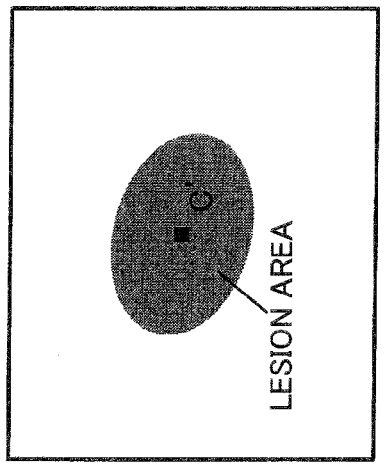
Figure 12D:
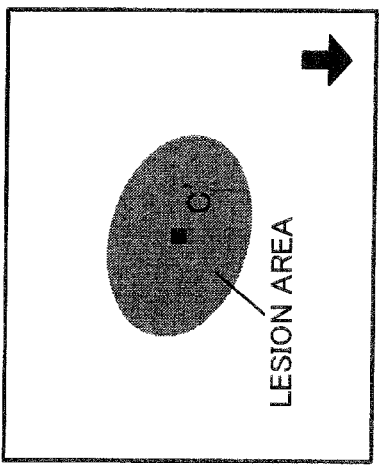

In the magnifying observation mode, the reference point setting section 351 acquires the coordinates (Xc', Yc') of a point C' (see FIG. 12A) positioned at the center of the image according to the mode information from the control section 360, and outputs the coordinates (Xc', Yc') to the distance estimation section 352 as the coordinate information about the reference point. The distance estimation section 352 calculates distance information Zc about the distance from the front focal distance to a point C on the object corresponding to the point C' in real space using the above method, and outputs the distance information Zc to the additional information generation section 356. Note that the reference point need not necessarily be the pixel positioned at the center of the image. An arbitrary pixel may be set as the reference point, or the reference point may be set by the doctor.

Figure 13A:
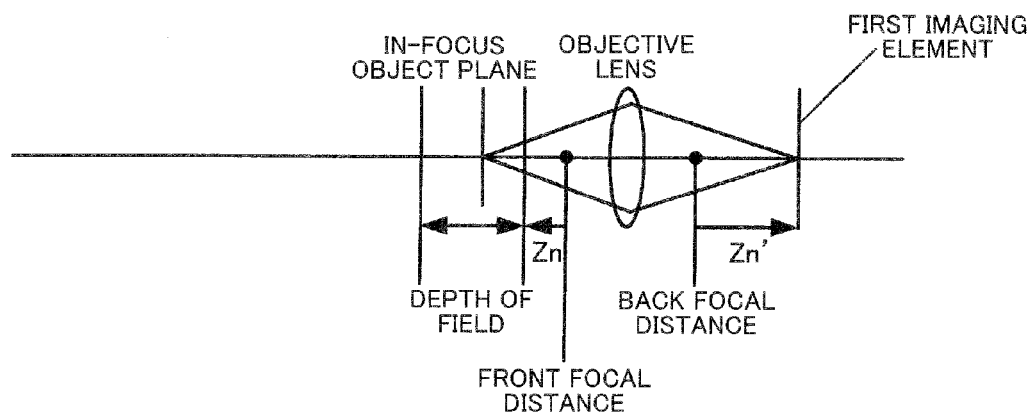
Figure 13B:
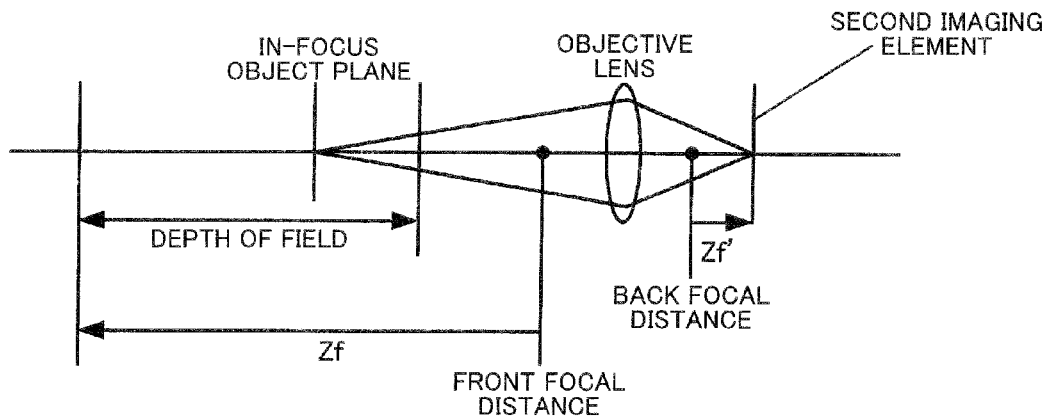

The additional information generation section 356 generates focus information from the distance information Zc output from the distance estimation section 352 according to the mode information from the control section 360. The focus information is generated as described below. The depth of field range of the near point image and the depth of field range of the far point image are known from the performance of the objective lens. As shown in FIG. 13A, the distance from the front focal distance of the optical system to the point within the depth of field range of the near point image that is closest to the objective lens is referred to as Zn. As shown in FIG. 13B, the distance from the front focal distance of the optical system to the point within the depth of field range of the far point image that is farthest from the objective lens is referred to as Zf.

It is considered that the depth of field range of the synthetic image obtained by synthesizing the near point image and the far point image is included within the depth of field range of the near point image or the depth of field range of the far point image. Therefore, the depth of field range of the synthetic image is within the range between the point at the distance Zn from the front focal distance and the point at the distance Zf from the front focal distance. The additional information generation section 356 compares the distance information Zc output from the distance estimation section 352 with the distance Zn and the distance Zf, and generates the following focus information, for example. The additional information generation section 356 then outputs the generated focus information to the process section 357.

Figure 14A:
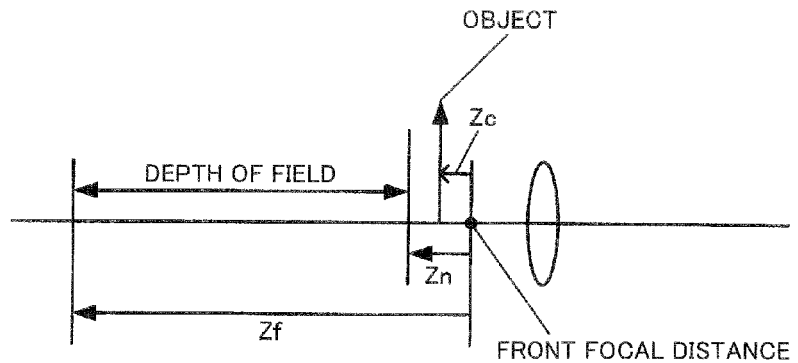
FIGS. 14A to 14C are views showing the relationship between the distances Zn and Zf and the distance Zc to an object.
Figure 14B:
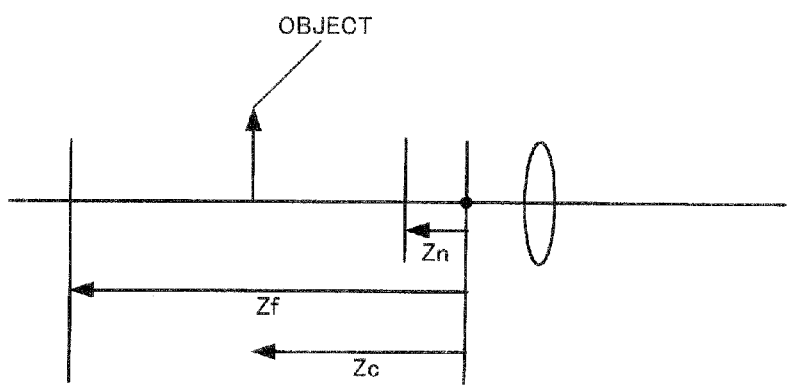
Figure 14C:
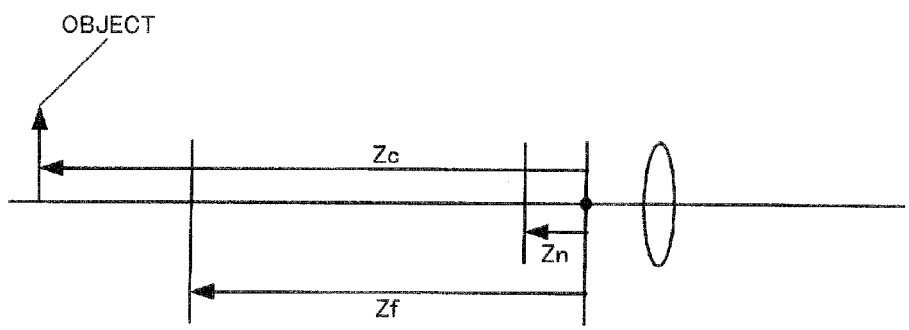

Examples of focus information (FIGS. 14A to 14C)

Zf>Zn>a: rear focus (i.e., the lesion area (i.e., object) is brought into focus by moving the imaging section backward)

Zf>Zc>Zn: in focus

Zc>Zf>Zn: front focus (i.e., the lesion area (i.e., object) is brought into focus by moving the imaging section forward)

Note that the focus information need not necessarily be calculated from the distance information Zc. For example, the distance estimation section 352 may directly output the contrast calculated by the contrast information calculation section 3522 to the additional information generation section 356, and the additional information generation section 356 may generate the focus information from the contrast information.

The process section 357 adds the focus information output from the additional information generation section 356 to the image output from the post-processing section 355 according to the mode information from the control section 360. For example, when the focus information "rear focus" is output from the additional information generation section 356, the process section 357 adds a downward arrow to the image as the focus information (see FIG. 12C). When the focus information "in focus" is output from the additional information generation section 356, the process section 357 adds a circle to the image as the focus information (see FIG. 12D). When the focus information "front focus" is output from the additional information generation section 356, the process section 357 adds an upward arrow to the image as the focus information (see FIG. 12E). This makes it possible for the doctor to easily determine the direction in which the imaging section 200 should be moved in order to bring the lesion area into focus, and easily bring the lesion area into focus.

The additional information generation section 356 may compare the distance information Zc output from the distance estimation section 352 with an arbitrary threshold value Zt, and may generate focus information "caution-prevent contact" when Zt>Zc. In this case, the process section 357 adds a cross mark to the image as the focus information (see FIG. 12B). This makes it possible for the doctor to determine that the imaging section 200 is positioned close to the lesion area, and prevent the imaging section 200 from coming in contact with the lesion area.

Note that an arbitrary symbol or character may be used as the focus information added to the image instead of an arrow, a circle, or a cross mark. It is also possible to use information such as arbitrary light or sound instead of adding the focus information to the image.

Figure 4:
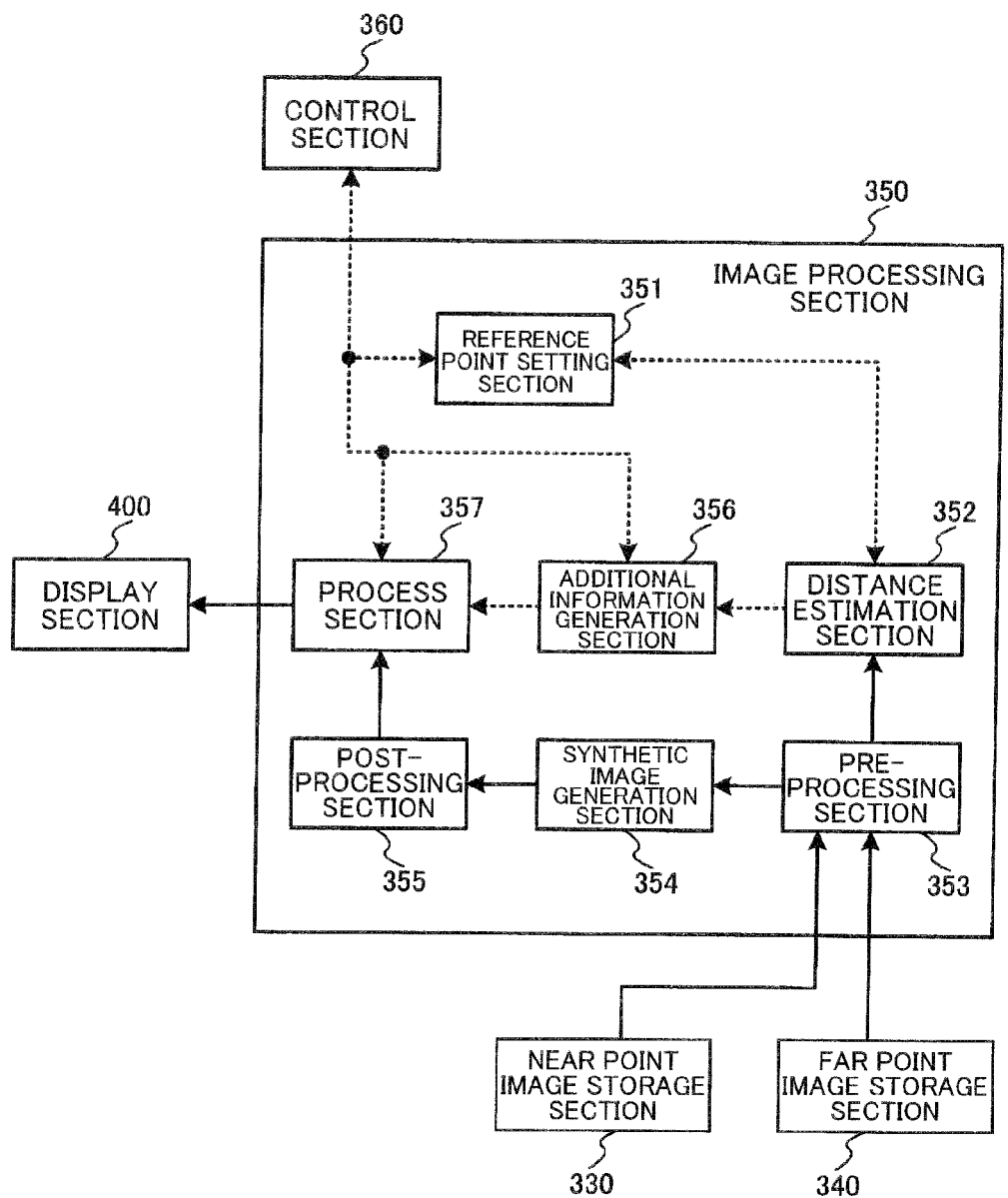
FIG. 4 shows a configuration example of an image processing section.

The image processing apparatus according to the first embodiment includes an image acquisition section (corresponding to the near point image storage section 330 and the far point image storage section 340 shown in FIG. 1) that acquires a plurality of images that differ in in-focus state, the reference point setting section 351 that performs a reference point setting process that sets a reference point that is set to an attention area, the distance estimation section 352 that estimates distance information about a distance to a corresponding point, the corresponding point being a point in real space that corresponds to the reference point, and the additional information generation section 356 that generates additional information based on the estimated distance information, the additional information being information that is added to the attention area to which the reference point is set (see FIGS. 1 and 4).

The expression "differ in in-focus state" means that the optical system differs in point of focus (in-focus object plane) (see FIGS, 3A and 3B). According to the first embodiment, the in-focus state is caused to differ by utilizing two imaging elements that differ in distance from the objective lens (see FIGS. 3A and 3B). Note that the method that implements a different in-focus state is not limited thereto. For example, a method that causes the in-focus object plane to differ corresponding to each channel (e.g., RGB) by increasing axial chromatic aberration may also be used (described later in connection with the second embodiment). A different in-focus state may also be implemented by driving a single imaging element (described later in connection with the third embodiment).

The term "attention area" refers to an area to which it is desired to add the additional information. For example, the attention area is an area for which the observation priority of the user is relatively higher than that of other areas. Specifically, when the user is a doctor, and desires to perform treatment, the attention area refers to an area that includes a mucosal area or a lesion area. Note that the attention area is not limited to a lesion area insofar as the attention area is an area for which the observation priority of the user is relatively higher than that of other areas.

The plurality of images are basically images of the same object. Therefore, the position of the attention area on each image has a correspondence relationship, and the position of the reference point set to each image also has a correspondence relationship. The correspondence relationship means that the coordinates of the attention area (reference point) on each image are identical, for example.

The starting point of the distance to the corresponding point is the front focal distance for the purpose of calculation. However, since the distance from the front focal distance to the lens is known from the design, the distance information about the distance to the corresponding point may be the distance information about the distance from the lens to the corresponding point.

The reference point setting process is a process that sets the coordinates (xd, yd) that indicate the position of the reference point on the image based on information that has been input by the user (doctor) and designates the position of the reference point. For example, when the user has designated a point positioned at x pixels sideways and y pixels downward from the upper left corner of the screen, the reference point setting process sets the coordinates of the reference point to (x, y), for example.

This makes it possible to estimate the distance information about the distance to the object (i.e., the corresponding point on the object) from a plurality of images that differ in in-focus state, and generate the additional information based on the estimated distance information. The additional information refers to the lesion size information (see FIG. 8C) or the like. The additional information facilitates diagnosis and treatment performed by the user (doctor).

Figure 5:
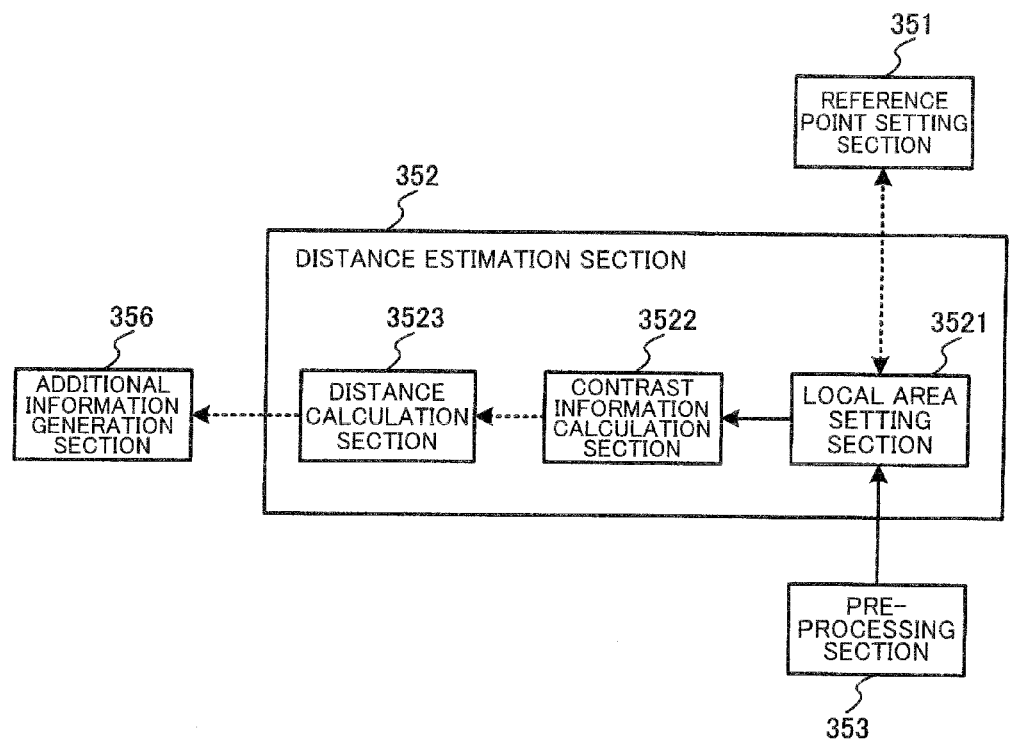
FIG. 5 shows a configuration example of a distance estimation section.
Figure 6:
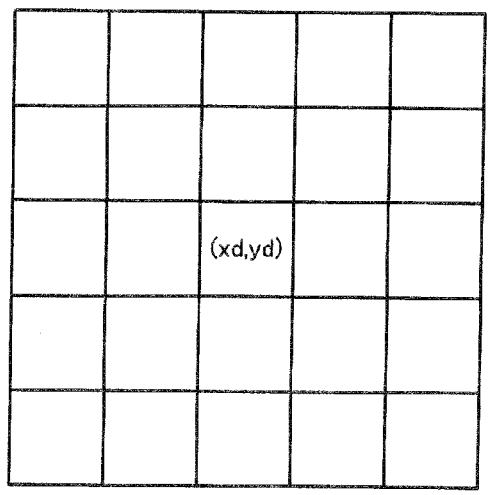
FIG. 6 shows a local area setting example.

As shown in FIG. 5, the image processing apparatus may include the contrast information calculation section 3522, and the distance estimation section 352 may estimate the distance information about the distance to the corresponding point based on the contrast information calculated by the contrast information calculation section 3522. Specifically, the distance information about the distance to the object may be estimated by calculating the distance information about the distance from the back focal distance to the focal position when the reference point is in focus. For example, the ratio of two pieces of contrast information calculated from two images, or the difference between two pieces of contrast information calculated from two images may also be used.

The distance information about the distance to the object can be estimated by utilizing a plurality of pieces of contrast information calculated from a plurality of images Specifically, the focal position is calculated from the contrast information calculated from an image (image in a first in-focus state in a broad sense) captured by the first imaging element and the contrast information calculated from an image (image in a second in-focus state in a broad sense) captured by the second imaging element (see FIG. 3). More specifically, the distance Z' is calculated from the ratio of two pieces of contrast information or the difference between two pieces of contrast information using a look-up table. The distance information Z about the distance to the object is calculated by the expression (1). The distance information Z may be calculated directly from the ratio of the contrast information or the difference between the contrast information using a function or the like. In this case, the distance Z' is essentially calculated. Therefore, the above method is also included within the scope of the method according to the first embodiment. The contrast information is not limited to the contrast calculated by the above method or another method, but may be information equivalent to the contrast.

The image processing apparatus may include an attention area detection section that detects the attention area. The reference point setting section 351 may perform the reference point setting process on the attention area detected by the attention area detection section.

This makes it possible to detect the attention area. In the first embodiment, a lesion area or the like found by the doctor during observation is detected as the attention area (see FIGS. 8A to 8E). Specifically, the attention area is basically detected by a manual operation of the doctor. Note that the configuration is not limited thereto. Specifically, a specific blood vessel structure or a lesion such as epidermoid cancer may be automatically detected as the attention area by special light observation such as narrow-band imaging (NBI).

The reference point setting section 351 may set first to Nth reference points to one attention area, the contrast information calculation section 3522 may calculate first to Nth contrast information corresponding to the first to Nth reference points, and the distance estimation section 352 may estimate first to Nth distance information based on the first to Nth contrast information.

Figure 8C:
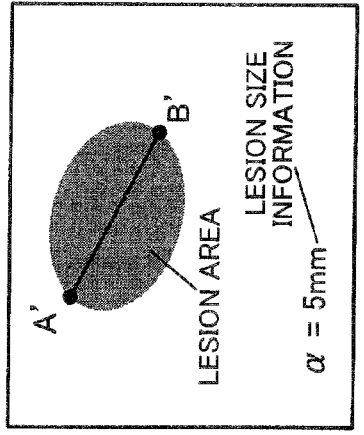
Figure 8B:
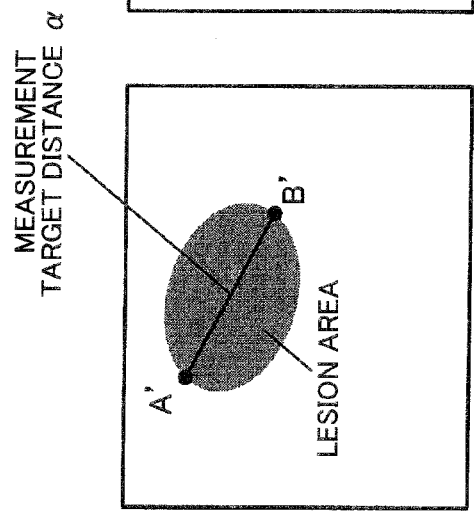
Figure 8A:
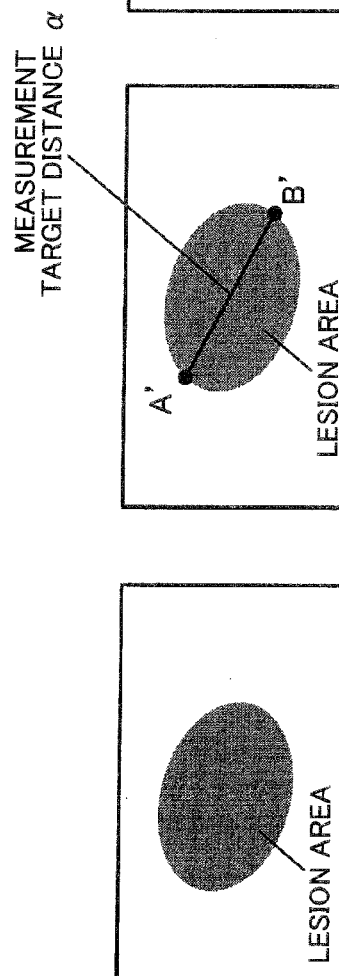

This makes it possible to set a plurality of reference points to one attention area (see FIGS. 8B and 8C). Therefore, the relationship between a plurality of reference points (i.e., a plurality of corresponding points) can be calculated.

The additional information generation section 356 may calculate the distance information about the distance between an ith corresponding point and a jth corresponding point in real space as the additional information based on ith distance information and jth distance information among the first to Nth distance information.

This makes it possible to calculate the distance between points corresponding to two points on the image in real space. Therefore, when a lesion area has been detected as shown in FIG. 8A, the size of the lesion area can be easily determined by designating two points on the lesion as shown in FIG. 8B.

The distance estimation section 352 estimates the distance Z indicated by the distance information about the distance to the corresponding point in real space that corresponds to the reference point. The additional information generation section 356 calculates the three-dimensional coordinates (X, Y, Z) of the corresponding point from the coordinates (X', Y') of the reference point on the image and the estimated distance Z. Note that the coordinate value Z of the corresponding point is indicated by the estimated distance information. Specifically, the coordinate values X and Y are calculated using the expressions (2) to (4).

This makes it possible to calculate the three-dimensional coordinates of the corresponding point in real space that corresponds to the reference point from the coordinates of the reference point on the image. Specifically, the three-dimensional coordinates are calculated based on the positional relationship shown in FIGS. 9A and 9B. The distance D from the front focal distance (origin) to the entrance pupil is known from the optical system design, and the angle $\theta b$ can be calculated from the image height Rb'. Since the Z-coordinate value Zb is the distance indicated by the estimated distance information, the position of the point B is determined as shown in FIG. 9B, and the distance Rb can be calculated (expression (2)). Since the angle from the X-axis to the point B is equal to the angle $\phi b$ from X'-axis to the point B', the coordinate values X and Y can be calculated using the expressions (3) and (4).

The reference point setting section 351 may set one reference point to one attention area. The contrast information calculation section 3522 may calculate the contrast information about the reference point, and the distance estimation section 352 may estimate the distance information about the distance to the corresponding point corresponding to the reference point based on the contrast information.

This makes it possible to set one reference point to one attention area. Specifically, the scale information or the like can be displayed as the additional information by designating only one point as the reference point (see FIG. 8D), so that an input operation of the user can be simplified.

The additional information generation section 356 may calculate the local magnification of the lens based on the distance information, and generate the scale information based on the local magnification. For example, the additional information generation section 356 may calculate the local magnification $\beta$ from the distance Z indicated by the distance information and the focal position f of the lens as indicated by "$\beta=\sqrt{(f^2/Z^2)}$". When the length of the scale in real space is referred to as L, the factor by the image process is referred to as βzoom, and the pixel pitch is referred to as P, the length of the scale on the image may be indicated by "L·β·βzoom/P (pixel)".

This makes it possible to generate the scale information from the local magnification of the lens. The local magnification β is indicated by the ratio of the size of the formed image to the size of the object (see FIG. 11). The local magnification β is calculated using the focal position f and the distance Z. The length of the scale on the image is calculated by multiplying the length L of the scale in real space by the local magnification β and the scaling factor βzoom, and dividing the resulting value by the pixel pitch P to determine the number of pixels.

The image processing apparatus may include an in-focus direction estimation section that estimates the in-focus direction based on the contrast information. The additional information generation section 356 may generate the indication information that indicates the estimated in-focus direction as the additional information.

Note that the term "in-focus direction" refers to a direction in which the imaging section should be moved in order to bring the object into focus. The in-focus direction is a forward direction when the object is brought into focus by moving the imaging section forward, and is a backward direction when the object is brought into focus by moving the imaging section backward.

This makes it possible to provide the user with the direction (additional information) in which the imaging section should be moved in order to bring the object into focus when the object is out of focus (i.e., Zf>Zn>Zc (FIG. 14A) or Zc>Zf>Zn (FIG. 14C)) (see FIGS. 12 C and 12E). According to this configuration, since the user can easily determine the in-focus direction, the user can smoothly perform an operation.

When the distance to the object is within a given range (i.e., Zf>Zc>Zn), the indication information that indicates that the object is in focus may be generated as the additional information.

According to this configuration, since the in-focus state can be displayed (e.g., a circle shown in FIG. 12D), the user need not perform an unnecessary focus adjustment or the like, so that the operability can be improved.

When the distance to the object has become equal to or shorter than a given threshold value, alert information may be generated as the additional information.

This makes it possible to display a contact alert or the like when the distance to the object is equal to or shorter than the threshold value (i.e., when the imaging section (included in an imaging apparatus or an endoscope system including the image processing apparatus according to the first embodiment) may come in contact with the object). In particular, since bleeding or the like may occur when an endoscope system comes in contact with a lesion area, the above configuration is useful. For example, a cross mark shown in FIG. 12B or the like is displayed as the contact alert.

The image acquisition section may acquire the plurality of images that differ in in-focus state by capturing a plurality of images while changing the position of the imaging element relative to the optical system.

This makes it possible to acquire the plurality of images that differ in in-focus state by changing the position of the imaging element. Specifically, the first embodiment utilizes a plurality of imaging elements that differ in distance from the lens, and the third embodiment described later changes the position of one imaging element by time division by driving the imaging element using an imaging element driver section 280.

The image processing apparatus according to the first embodiment may include an image acquisition section that acquires a plurality of images that differ in in-focus state, the reference point setting section 351 that performs a reference point setting process on each of the plurality of images, the reference point setting process setting a reference point that is set to an attention area, the contrast information calculation section 3522 that calculates contrast information about the reference point based on a pixel value of a pixel of the reference point, and the distance estimation section 352 that estimates distance information about a distance to a corresponding point, the corresponding point being a point in real space that corresponds to the reference point.

The distance information about the distance to the corresponding point in real space that corresponds to the reference point can be estimated by acquiring a plurality of images that differ in in-focus state, setting the reference point to the attention area included in each image, and calculating the contrast information about the reference point. For example, the distance information may be estimated from the ratio of a plurality of pieces of contrast information or the difference between a plurality of pieces of contrast information.

The first embodiment may be applied to an image processing method including acquiring a plurality of images that differ in in-focus state, performing a reference point setting process on each of the plurality of images, the reference point setting process setting a reference point that is set to an attention area, estimating distance information about a distance to a corresponding point based on a pixel value corresponding to the reference point, the corresponding point being a point in real space that corresponds to the reference point, and generating additional information based on the estimated distance information.

This makes it possible to achieve the above effects by applying the method according to the first embodiment to an image processing method instead of an endoscope system.

The first embodiment may be applied to an imaging apparatus including an image acquisition section (corresponding to the near point image storage section 330 and the far point image storage section 340 shown in FIG. 1) that acquires a plurality of images that differ in in-focus state, the reference point setting section 351 that sets a reference point to an attention area, the distance estimation section 352 that estimates distance information about a distance to a corresponding point, the corresponding point being a point in real space that corresponds to the reference point, and the additional information generation section 356 that generates additional information based on the estimated distance information, the additional information being information that is added to the attention area to which the reference point is set (see FIGS. 1 and 4), This makes it possible to achieve the above effects by applying the method according to the first embodiment to an imaging apparatus including the image processing apparatus according to the first embodiment, for example.

The first embodiment may also be applied to a program that causes a computer to function as the image acquisition section, the reference point setting section 351, the distance estimation section 352, and the additional information generation section 356. The image acquisition section acquires a plurality of images that differ in in-focus state, and the reference point setting section 351 sets a reference point to an attention area. The distance estimation section 352 estimates the distance information about the distance to the corresponding point in real space that corresponds to the reference point, and the additional information generation section 356 generates the additional information based on the distance information.

This makes it possible to apply the first embodiment to a system (e.g., imaging apparatus and endoscope system) that acquires an image, and process the image, and a system that stores image data, and processes the stored image data by software using a computer system (e.g., PC), for example.

3. Second Embodiment

Figure 15:
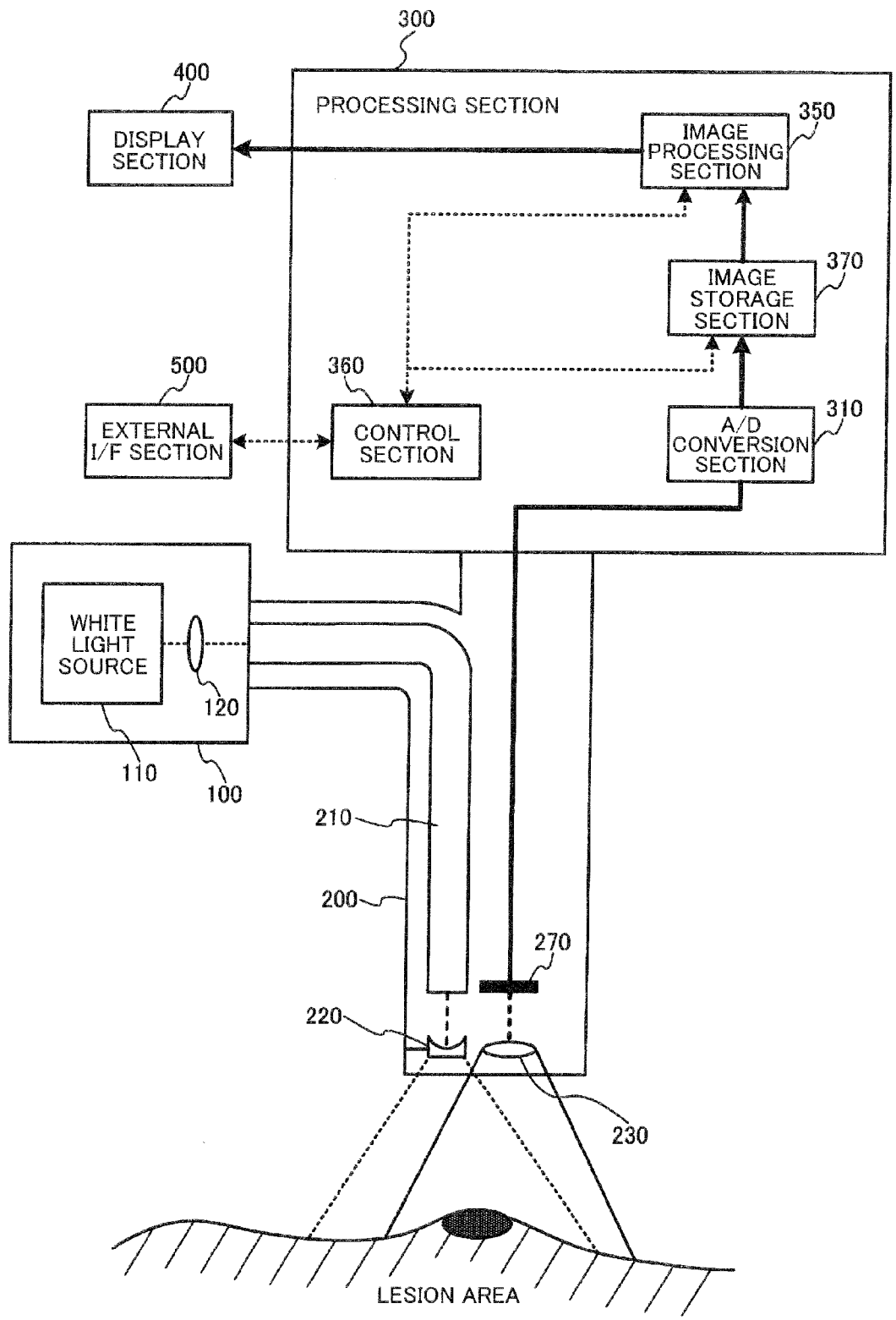
FIG. 15 shows another system configuration example according to one embodiment of the invention.

An endoscope system including an image processing apparatus according to the second embodiment of the invention is described below with reference to FIG. 15. The endoscope system according to the second embodiment includes a light source section 100, an imaging section 200, a processing section 300, a display section 400, and an external I/F section 500.

The light source section 100 includes a white light source 110 that emits (generates) white light, and a condenser lens 120 that focuses white light on a light guide fiber 210.

The imaging section 200 is formed to be elongated and flexible (i.e., can be curved) so that the imaging section 200 can be inserted into a body cavity or the like. The imaging section 200 includes the light guide fiber 210 that guides light focused by the light source section 100, an illumination lens 220 that diffuses light that has been guided by the light guide fiber 210, and illuminates an observation target, an objective lens 230 that focuses light reflected by the observation target, and an imaging element 270. The imaging element 270 includes a Bayer color filter array shown in FIG. 2, and color filters Gr and Gb have the same spectral characteristics.

Figure 16A:
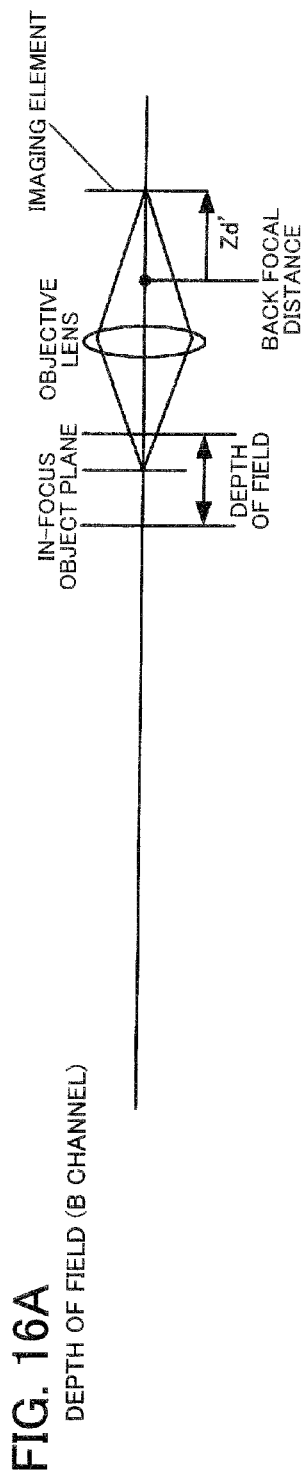
FIG. 16A to 16C are views illustrative of the depth of field corresponding to each channel (RGB).
Figure 16B:
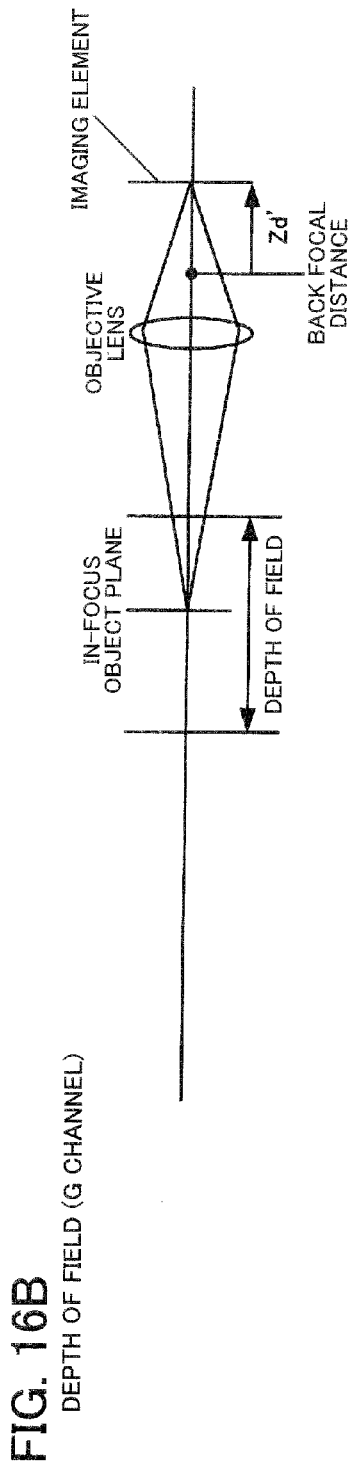
Figure 16C:
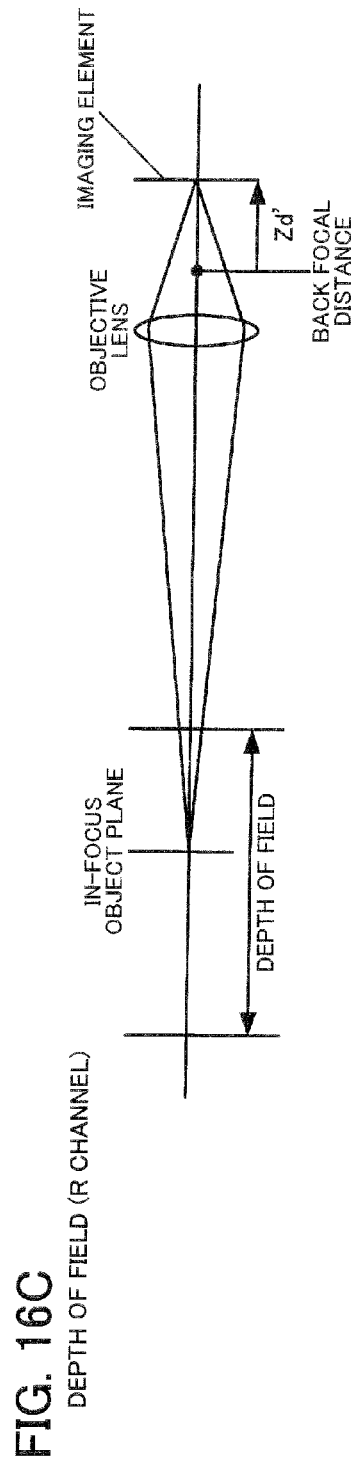
Figure 17:
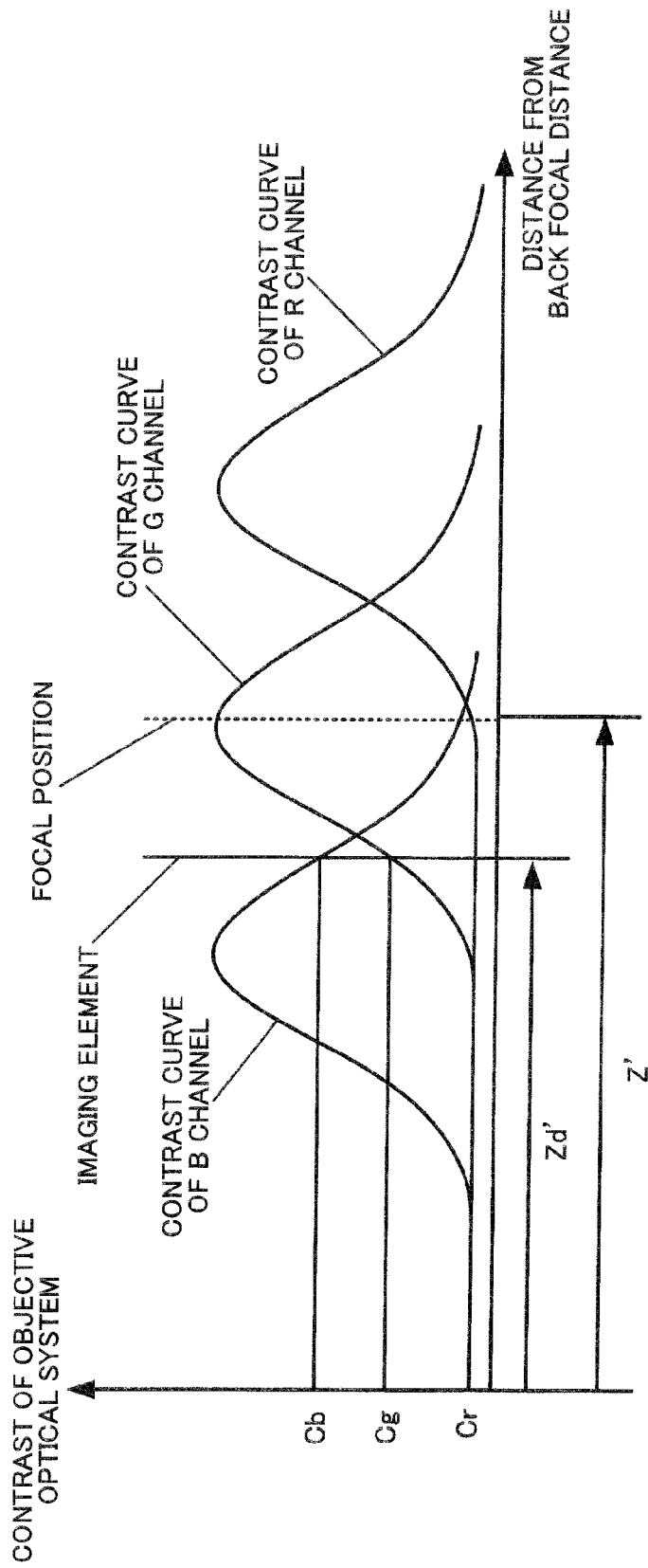
FIG. 17 is a view showing the relationship between the distance from the back focal distance of an objective lens and the contrast of the objective lens at a given spatial frequency.

The depth of field of an image acquired (captured) corresponding to each channel of the imaging element is described below with reference to FIGS. 16A to 16C and 17. FIGS. 16A to 16C show examples of a contrast curve corresponding to each channel (RGB) that indicates the relationship between the distance from the back focal distance and the contrast of the objective lens at a given spatial frequency. The objective lens used in connection with the second embodiment is designed to produce large axial chromatic aberration. Therefore, the position where the highest contrast is obtained differs depending on the channel. Therefore, the depth of field range of an image acquired corresponding to each channel differs depending on the channel (see FIGS. 16A to 16C). In FIGS. 16A to 16C, the depth of field range becomes closer to the objective lens in the order of the R channel, the G channel, and the B channel. The depth of field of an image acquired corresponding to each channel can be adjusted by adjusting the amount of axial chromatic aberration of the objective lens and the distance Zd' from the back focal distance of the objective lens to the imaging element 270.

The processing section 300 includes an A/D conversion section 310, an image storage section 370, an image processing section 350, and a control section 360. The A/D conversion section 310 converts an analog signal output from the imaging element 270 into a digital signal, and outputs the digital signal. The image storage section 370 stores the digital signal output from the A/D conversion section 310 as an image. The image processing section 350 generates a display image from the image stored in the image storage section 370, and displays the display image on the display section 400. The details of the image processing section 350 are described later. The display section 400 is a liquid crystal monitor, for example. The display section 400 displays the image output from the image processing section 350. The control section 360 is bidirectionally connected to the image storage section 370 and the image processing section 350, and controls the image storage section 370 and the image processing section 350.

The external I/F section 500 is an interface that allows the user to perform an input operation or the like on the imaging apparatus. The external I/F section 500 includes a power supply switch (power supply ON/OFF switch), a shutter button (photographing operation start button), a mode (e.g., photographing mode) change button, and the like. The external IN section 500 outputs information input by the user to the control section 360.

Figure 18:
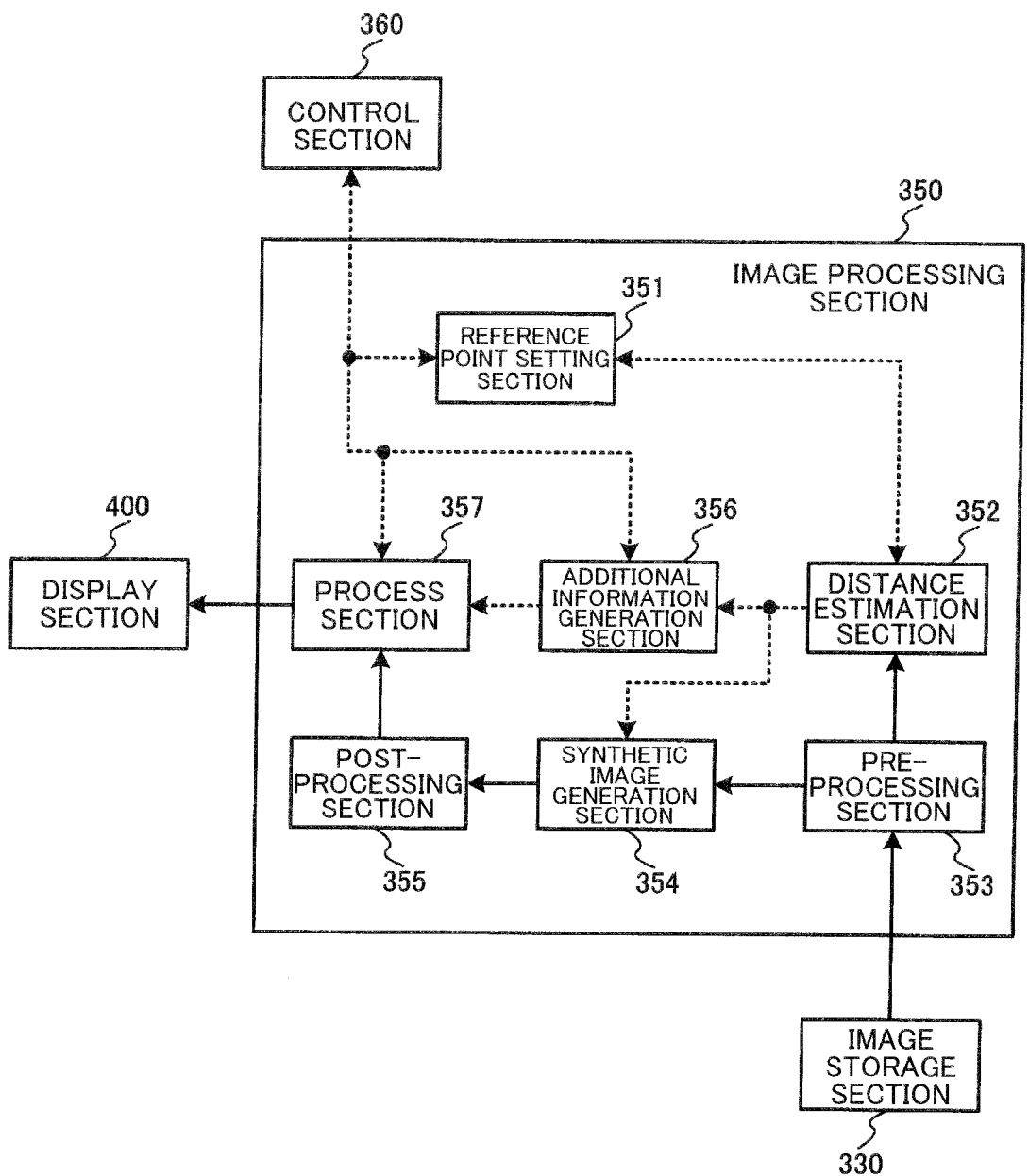
FIG. 18 shows another configuration example of an image processing section.

The details of the image processing section 350 are described below with reference to FIG. 18. The image processing section 350 includes a reference point setting section 351, a distance estimation section 352, a preprocessing section 353, a synthetic image generation section 354, a post-processing section 355, an additional information generation section 356, and a process section 357. The reference point setting section 351 outputs information about a distance estimation target position on the image to the distance estimation section 352 as coordinate information about a reference point based on a control signal from the control section 360.

The preprocessing section 353 performs a preprocess (e.g., OB process, white balance process, and demosaicing process) on the image stored in the image storage section 370, and outputs the resulting image to the distance estimation section 352 and the synthetic image generation section 354. The preprocessing section 353 may optionally perform a correction process on optical aberration (e.g., distortion and chromatic aberration of magnification), a noise reduction process, and the like.

The distance estimation section 352 estimates the distance to the object in real space by utilizing the image output from the preprocessing section 353 based on the coordinate information about the reference point output from the reference point setting section 351, and outputs the distance information or the distance information and the coordinate information about the reference point to the additional information generation section 356. The details of the distance estimation section 352 are described later. The additional information generation section 356 generates additional information using the distance information or the distance information and the coordinate information about the reference point output from the distance estimation section 352 based on a control signal from the control section 360, and outputs the additional information to the process section 357. The details of the additional information generation section 356 are described later.

The synthetic image generation section 354 generates a synthetic image with an increased depth of field from the image output from the preprocessing section 353, and outputs the synthetic image to the post-processing section 355. The synthetic image generation section 354 generates the synthetic image with an increased depth of field using the method disclosed in Reference 2, for example. The post-processing section 355 performs a post-process (e.g., color conversion process, grayscale transformation process, edge enhancement process, and scaling process) on the synthetic image output from the synthetic image generation section 354, and outputs the resulting image to the process section 357.

The process section 357 processes the image output from the post-processing section 355 using the additional information output from the additional information generation section 356 based on control information from the control section 360, and outputs the resulting image to the display section 400.

The details of the process performed by the distance estimation section 352 are described below with reference to FIG. 5. The distance estimation section 352 includes a local area setting section 3521, a contrast information calculation section 3522, and a distance calculation section 3523. The local area setting section 3521 sets a local area to an image input from the preprocessing section 353 based on the coordinates of the reference point output from the reference point setting section 351. For example, the local area setting section 3521 sets a 3×3 pixel area around the coordinates (xd, yd) of the reference point as the local area of each image. The contrast information calculation section 3522 calculates contrast (Cr, Cg, and Cb) corresponding to each channel from the local area set to the image, and outputs the calculated contrast to the distance calculation section. For example, the contrast information calculation section 3522 calculates gradients Δu, Δd, Δl, and Δr of each pixel of the local area relative to four pixels adjacent to each pixel in the vertical direction or the horizontal direction in each channel, and calculates the average values Δave_R, Δave_G, and Δave_B of the gradients of each pixel of the local area in the four directions to determine the contrast Cr, the contrast Cg, and the contrast Cb. The contrast information calculation section 3522 may calculate the average value of the edge strength of the local area as the contrast corresponding to each channel, for example.

The distance calculation section 3523 calculates the distance to the object corresponding to the reference point. A distance calculation method is described below with reference to FIG. 17. If the distance Z' from the back focal distance to the focal position of the object corresponding to the reference point is determined, the distance Z from the front focal distance to the object corresponding to the reference point can be calculated by the following expression (1).

$$Z \cdot Z' = -f^2 \quad (1)$$

Since the contrast curve of the objective lens is known from the design data, the distance Z' can be calculated using at least two of the contrast Cr, the contrast Cg, and the contrast Cb. For example, the relationship between the contrast ratio Cg/Cb of the G channel to the B channel and the corresponding distance Z' may be stored as a look-up table, or a function G(x) that approximates the distance Z' as indicated by Z'=G (Cg/Cb) (i.e., a function of the contrast ratio Cg/Cb) may be set in advance. Note that the contrast ratio Cg/Cr of the G channel to the R channel or the contrast ratio Cb/Cr of the B channel to the R channel may be used instead of the contrast ratio Cg/Cb. Alternatively, a function h(x, y) that approximates the distance Z' as indicated by Z'=h(Cg/Cb, Cg/Cr) may be set in advance, for example.

The distance calculation section 3523 can calculate the distance to the object corresponding to the reference point from the contrast Cn and the contrast Cf by performing the above process. The distance Z can be uniquely calculated by the expression (1) when the distance Z' has been calculated. For example, the relationship between the contrast ratio Cg/Cb and the distance Z to the corresponding object may be stored directly as a look-up table, or a function i(x) that approximates the distance Z as indicated by Z=i(Cg/Cb) (i.e., a function of the contrast ratio Cg/Cb) may be set in advance. The contrast difference Cg−Cb or the like may be used as a parameter for calculating the distance Z' or Z instead of the contrast ratio Cg/Cb of the G channel to the B channel.

It is possible to provide a doctor with a diagnostic value in the same manner as in the first embodiment by utilizing the distance information calculated by the distance estimation section 352.

4. Third Embodiment

Figure 19:
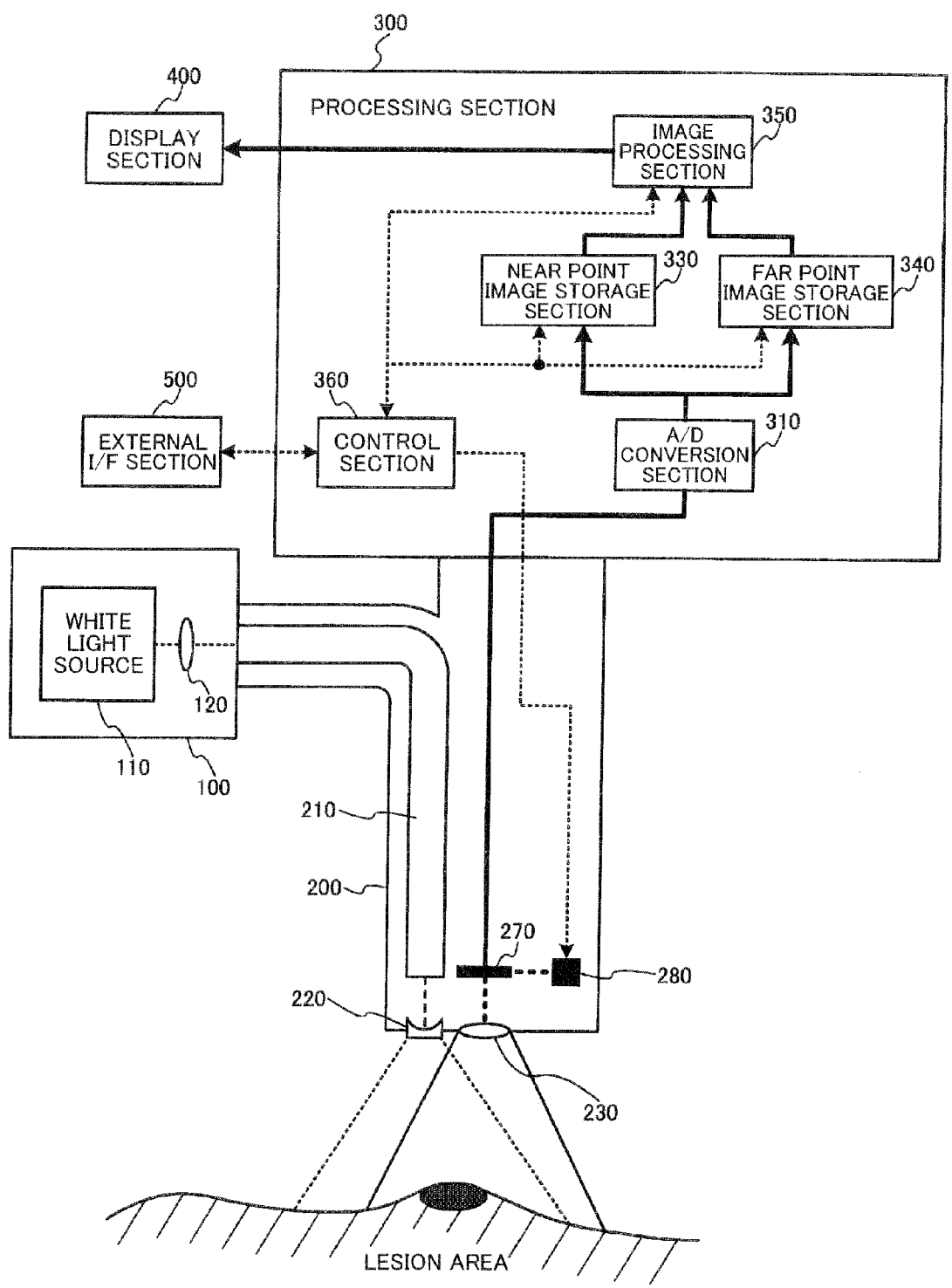
FIG. 19 shows another system configuration example according to one embodiment of he invention.

An endoscope system including an image processing apparatus according to the third embodiment of the invention is described below with reference to FIG. 19. The endoscope system according to the third embodiment includes a light source section 100, an imaging section 200, a processing section 300, a display section 400, and an external I/F section 500.

The light source section 100 includes a white light source 110 that emits (generates) white light, and a condenser lens 120 that focuses white light on a light guide fiber 210.

The imaging section 200 is formed to be elongated and flexible (i.e., can be curved) so that the imaging section 200 can be inserted into a body cavity or the like. The imaging section 200 includes the light guide fiber 210 that guides light focused by the light source section 100, an illumination lens 220 that diffuses light that has been guided by the light guide fiber 210, and illuminates an observation target, an objective lens 230 that focuses light reflected by the observation target, an imaging element 270, and an imaging element driver section 280 that drives the imaging element 270. The imaging element 270 includes a Bayer color filter array shown in FIG. 2, and color filters Gr and Gb have the same spectral characteristics.

The imaging element driver section 280 moves the imaging element 270 under control of the control section 360 so that the imaging element 270 is set in a first imaging state or a second imaging state. The first imaging state refers to a state in which the distance from the objective lens (or the distance from the back focal distance) is longer than that in the second imaging state. Specifically, while the first embodiment acquires two images that differ in in-focus state using the first imaging element 250 and the second imaging element 260, the third embodiment acquires two images that differ in in-focus state by driving (moving) one imaging element.

The processing section 300 includes an A/D conversion section 310, a near point image storage section 330, a far point image storage section 340, an image processing section 350, and a control section 360. The A/D conversion section 310 converts an analog signal output from the imaging element 270 into a digital signal, and outputs the digital signal. The A/D conversion section 310 outputs the digital signal to the near point image storage section 330 when the imaging element 270 is set in the first imaging state, and outputs the digital signal to the far point image storage section 340 when the imaging element 270 is set in the second imaging state, based on a control signal from the control section 360. The near point image storage section 330 stores the digital signal output from the A/D conversion section 310 as a near point image. The far point image storage section 340 stores the digital signal output from the A/D conversion section 310 as a far point image. The image processing section 350 generates a display image from the stored near point image and far point image, and displays the display image on the display section 400. The details of the image processing section 350 are the same as described above. The control section 360 is bidirectionally connected to the near point image storage section 330, the far point image storage section 340, and the image processing section 350, and controls the near point image storage section 330, the far point image storage section 340, and the image processing section 350.

The process after the near point image and the far point image have been acquired is the same as described above in connection with the first embodiment. Therefore, detailed description thereof is omitted.

According to the third embodiment, since a plurality of images that differ in in-focus state can be acquired even if only one imaging element is used, the distance estimation and the additional information can be generated.

The first to third embodiments according to the invention and the modifications thereof have been described above. Note that the invention is not limited to the first to third embodiments and the modifications thereof. Various modifications and variations may be made without departing from the scope of the invention. A plurality of elements of each of the first to third embodiments and the modifications thereof may be appropriately combined. For example, an arbitrary element may be omitted from the first to third embodiments and the modifications thereof. Some of the elements described in connection with the first to third embodiments and the modifications thereof may be appropriately combined. Specifically, various modifications and applications are possible without materially departing from the novel teachings and advantages of the invention.

What is claimed is:

1. An image processing apparatus comprising:
   a processor; and
   a memory storing computer readable instructions that, when executed by the processor, implement:
   an image acquisition section that acquires a plurality of images that differ in in-focus state through an objective lens;
   a reference point setting section that performs a reference point setting process on each of the plurality of images, the reference point setting process setting a reference point that is set to an attention area;
   a contrast information calculation section that calculates a contrast of each of at least two images among the plurality of images in an area corresponding to the reference point;
   a distance estimation section that estimates distance information about a distance to a corresponding point based on the contrast of each of the at least two images, and a contrast curve that indicates a relationship between a distance from the objective lens and a contrast of the objective lens at an arbitrary spatial frequency, the corresponding point being a point in real space that corresponds to the reference point; and
   an additional information generation section that generates additional information based on the estimated distance information, the additional information being information that is added to the attention area to which the reference point is set.

2. The image processing apparatus as defined in claim 1, the distance estimation section estimating the distance information about the distance to the corresponding point in real space that corresponds to the reference point by calculating distance information about a distance from a back focal distance to a focal position when the reference point is in focus based on the calculated contrast information.

3. The image processing apparatus as defined in claim 2, the distance estimation section estimating the distance information about the distance to the corresponding point in real space that corresponds to the reference point based on a ratio of first contrast information to second contrast information or a difference between the first contrast information and the second contrast information, the first contrast information being calculated corresponding to a first image among the plurality of images, and the second contrast information being calculated corresponding to a second image among the plurality of images.

4. The image processing apparatus as defined in claim 1, the reference point setting section setting first to Nth (N is an integer equal to or larger than 2) reference points to one attention area,
   the contrast information calculation section calculating first to Nth contrast information corresponding to the first to Nth reference points, and
   the distance estimation section estimating first to Nth distance information about a distance to each of first to Nth corresponding points in real space respectively corresponding to the first to Nth reference points based on the calculated first to Nth contrast information.

5. The image processing apparatus as defined in claim 4, the additional information generation section calculating distance information about a distance between an ith ($1 \leq i \leq N$) corresponding point and a jth ($1 \leq j \leq N$, $i \neq j$) corresponding point in real space as the additional information based on ith distance information and jth distance information among the first to Nth distance information, the ith distance information being calculated from an ith reference point among the first to Nth reference points, and the jth distance information being calculated from a jth reference point among the first to Nth reference points.

6. The image processing apparatus as defined in claim 1, wherein the computer readable instructions, when executed by the processor, implement an attention area detection section that detects the attention area that is an area corresponding to an addition process of the additional information,
   the reference point setting section performing the reference point setting process on the attention area detected by the attention area detection section.

7. The image processing apparatus as defined in claim 1, the distance estimation section estimating a distance Z that is indicated by the distance information about the distance to the corresponding point in real space that corresponds to the reference point, and
   the additional information generation section calculating coordinate values X and Y of three-dimensional coordinates (X, Y, Z) of the corresponding point corresponding to the reference point based on coordinates (X', Y') of the reference point on the image and the distance Z to the corresponding point.

8. The image processing apparatus as defined in claim 7, the additional information generation section calculating the coordinate values X and Y of the three-dimensional coordinates (X, Y, Z) of the corresponding point using the following expressions "$R=(Z+D)/\tan(\pi/2-\theta)$", "$X=R\cdot\cos\phi$", and "$Y=R\cdot\sin\phi$", when a distance from an image center to the reference point is referred to as R, an angle formed by a straight line that passes through the reference point and the image center and an axis parallel to a horizontal direction of the image is referred to as $\phi$, an angle at which a beam emitted from the corresponding point in real space enters an entrance pupil is referred to as $\theta$, and a distance from the entrance pupil to a front focal distance is referred to as D.

9. The image processing apparatus as defined in claim 1, the reference point setting section setting one reference point to one attention area,
   the contrast information calculation section calculating the contrast information about the reference point set by the reference point setting section, and
   the distance estimation section estimating the distance information about a distance to a corresponding point in real space that corresponds to the reference point based on the calculated contrast information.

10. The image processing apparatus as defined in claim 9,
the additional information generation section calculating a local magnification of a lens included in an optical system based on the estimated distance information, and generating scale information based on the local magnification.

11. The image processing apparatus as defined in claim 10,
the distance estimation section estimating a distance Z that is indicated by the distance information about the distance to the corresponding point in real space that corresponds to the reference point, and
the additional information generation section calculating the local magnification β from the estimated distance Z and a focal length f of an objective lens as indicated by "β=√(f²/Z²)".

12. The image processing apparatus as defined in claim 11,
the additional information generation section calculating a length of a scale on the image as indicated by "L·β·βzoom/P" when displaying the scale information having a length of L in real space, when a scaling factor by an image process is referred to as βzoom, and a pixel pitch of an imaging element is referred to as P.

13. The image processing apparatus as defined in claim 1, wherein the computer readable instructions, when executed by the processor, implement an in-focus direction estimation section that estimates an in-focus direction based on contrast information calculated corresponding to each of the plurality of images,
the additional information generation section generating indication information that indicates the estimated in-focus direction as the additional information.

14. The image processing apparatus as defined in claim 1,
the additional information generation section generating indication information that indicates that an object is in focus as the additional information when a distance indicated by the distance information about the distance to the corresponding point corresponding to the reference point is within a given range.

15. The image processing apparatus as defined in claim 1,
the additional information generation section generating alert information as the additional information when a distance indicated by the distance information about the distance to the corresponding point corresponding to the reference point has become equal to or shorter than a given threshold value.

16. The image processing apparatus as defined in claim 1,
the image acquisition section acquiring the plurality of images that differ in in-focus state by capturing a plurality of images while changing a position of an imaging element relative to an optical system.

17. An image processing apparatus comprising:
a processor; and
a memory storing computer readable instructions that, when executed by the processor, implement:
an image acquisition section that acquires a plurality of images that differ in in-focus state through an objective lens;
a reference point setting section that performs a reference point setting process on each of the plurality of images, the reference point setting process setting a reference point that is set to an attention area;
a contrast information calculation section that calculates a contrast of each of at least two images among the plurality of images in an area corresponding to the reference point; and
a distance estimation section that estimates distance information about a distance to a corresponding point based on the contrast of each of the at least two images, and a contrast curve that indicates a relationship between a distance from the objective lens and a contrast of the objective lens at an arbitrary spatial frequency, the corresponding point being a point in real space that corresponds to the reference point.

18. An image processing method comprising:
acquiring a plurality of images that differ in in-focus state through an objective lens;
performing a reference point setting process on each of the plurality of images, the reference point setting process setting a reference point that is set to an attention area;
calculating a contrast of each of at least two images among the plurality of images in an area corresponding to the reference point;
estimating distance information about a distance to a corresponding point based on the contrast of each of the at least two images, and a contrast curve that indicates a relationship between a distance from the objective lens and a contrast of the objective lens at an arbitrary spatial frequency, the corresponding point being a point in real space that corresponds to the reference point; and
generating additional information based on the estimated distance information, the additional information being information that is added to the attention area to which the reference point is set.

19. An imaging apparatus comprising:
a processor; and
a memory storing computer readable instructions that, when executed by the processor, implement:
an image acquisition section that acquires a plurality of images that differ in in-focus state through an objective lens;
a reference point setting section that performs a reference point setting process on each of the plurality of images, the reference point setting process setting a reference point that is set to an attention area;
a contrast information calculation section that calculates a contrast of each of at least two images among the plurality of images in an area corresponding to the reference point;
a distance estimation section that estimates distance information about a distance to a corresponding point based on the contrast of each of the at least two images, and a contrast curve that indicates a relationship between a distance from the objective lens and a contrast of the objective lens at an arbitrary spatial frequency, the corresponding point being a point in real space that corresponds to the reference point; and
an additional information generation section that generates additional information based on the estimated distance information, the additional information being information that is added to the attention area to which the reference point is set.

20. An information storage medium storing a program that causes a computer to function as:
an image acquisition section that acquires a plurality of images that differ in in-focus state through an objective lens;
a reference point setting section that performs a reference point setting process on each of the plurality of images, the reference point setting process setting a reference point that is set to an attention area;
a contrast information calculation section that calculates a contrast of each of at least two images among the plurality of images in an area corresponding to the reference point;

a distance estimation section that estimates distance information about a distance to a corresponding point based on the contrast of each of the at least two images, and a contrast curve that indicates a relationship between a distance from the objective lens and a contrast of the objective lens at an arbitrary spatial frequency, the corresponding point being a point in real space that corresponds to the reference point; and an additional information generation section that generates additional information based on the estimated distance information, the additional information being information that is added to the attention area to which the reference point is set.

\* \* \* \* \*